United States Patent [19]
Satake et al.

[11] Patent Number: 5,470,816
[45] Date of Patent: Nov. 28, 1995

[54] THERMAL RECORDING SHEET

[75] Inventors: Toshimi Satake; Toshiyuki Takano; Hideki Hayasaka; Yukiko Uehori; Tomoaki Nagai, all of Tokyo, Japan

[73] Assignee: Nippon Paper Industries Co., Ltd., Tokyo, Japan

[21] Appl. No.: 267,903

[22] Filed: Jul. 6, 1994

[30] Foreign Application Priority Data

| Jul. 8, 1993 | [JP] | Japan | 5-169244 |
| Dec. 13, 1993 | [JP] | Japan | 5-311502 |

[51] Int. Cl.$^6$ ..................... B41M 5/30
[52] U.S. Cl. .................. 503/201; 503/216; 503/225
[58] Field of Search .................. 427/150–152; 503/201, 212, 216, 217, 221, 226

[56] References Cited

U.S. PATENT DOCUMENTS

| 5,260,253 | 11/1993 | Kawakami et al. | 503/216 |

FOREIGN PATENT DOCUMENTS

| 55-164385 | 11/1980 | Japan | 503/216 |
| 57-94268 | 6/1982 | Japan | 503/216 |
| 57-176747 | 10/1982 | Japan | 503/209 |
| 58-58893 | 1/1983 | Japan | 503/216 |
| 58-58894 | 4/1983 | Japan | 503/216 |
| 59-50069 | 3/1984 | Japan | 503/221 |
| 59-115233 | 6/1984 | Japan | 503/216 |
| 60-53078 | 3/1985 | Japan | 503/216 |
| 62-53483 | 3/1987 | Japan | 503/208 |
| 649059 | 1/1989 | Japan | 503/201 |
| 649058 | 1/1989 | Japan | 503/201 |
| 225079 | 2/1990 | Japan | 503/201 |
| 3129568 | 5/1991 | Japan | 503/209 |
| 3168698 | 6/1991 | Japan | 503/201 |
| 3300491 | 11/1991 | Japan | 503/216 |
| 4111286 | 4/1992 | Japan | 503/216 |

OTHER PUBLICATIONS

Rewritable Thermal Recording Material, Yasuro Yokota et al. Mitsubishi Paper Mills Ltd., Tukuba Res. Labs, 46 Wadai, Tsukuba, Ibaraki, 300–42 Japan.

Recent trends of reuse of recording paper and reversible recording media, Eiichi Kawamura, Chemical Products R & D Center Ricoh Company, Ltd.

*Primary Examiner*—B. Hamilton Hess
*Attorney, Agent, or Firm*—Sherman & Shalloway

[57] ABSTRACT

In a thermal recording sheet having a thermal recording layer containing a colorless or pale colored dye precursor and a color developer reactable with the dye precursor upon heating to develop a color, a dimerized or trimerized urea compound is used as the color developer to obtain a thermal recording sheet which is superior in ground color stability and a thermal recording sheet having a reversible recordability.

15 Claims, No Drawings

THERMAL RECORDING SHEET

FIELD OF THE INVENTION

This invention relates to a thermal recording sheet with improved stability of the ground color and to a thermal recording sheet having a reversible recording ability with a bright color tone.

DESCRIPTION OF THE PRIOR ART

In general, to obtain a thermal recording sheet, a colorless or pale colored electron-donating dye and a color developer such as phenolic compounds are individually pulverized to fine particles, mixed with each other, and a binder, a filler, a sensitizer, a slip agent, and other additives are added to obtain a coating color, which is coated on a substrate such as paper, synthetic paper, films, plastics, or the like. The coated sheet is color developed by an instantaneous chemical reaction by heating with a thermal head, a hot stamp, laser light, or the like to obtain a visible record.

The thermal recording sheet is used in a wide variety of applications such as measuring recorders, a terminal printer for computers, facsimile, automatic ticket vendors, bar-code labels, and the like. However, with recent diversification and advance in recording apparatus for thermal recording sheet, the thermal recording sheet is required to meet increased requirements. For example, with increasing speed of recording, it is required to obtain a high-density and sharp color image even with a smaller thermal energy, whereas, in view of storage stability of the recording sheet, it is required to have improved light resistance, oil resistance, water resistance, and solvent resistance.

On the other hand, with increasing use of systems for recording on plain paper such as electrophotographic and ink jet recording systems, thermal recording becomes often compared with such plain paper recording. For example, thermal recording is required to be close in quality to plain paper recording in terms of stability of recorded portion (image) and stability of unrecorded portion (ground color portion) before and after recording (hereinafter referred to as ground color stability). In particular, as a basic function of thermal recording, the sheet is required to have a good ground color stability to heat and solvents, that is, the sheet is desired to be heat-sensitive only during recording, but non-sensitive in other times.

For the ground color stability of thermal recording sheet, for example, Japanese Patent Laid-open Publication (OPI) 4-353490 discloses a thermal recording sheet which undergoes no deterioration in the whiteness of ground color even at high temperatures of about 95° C. This thermal recording sheet contains 4-hydroxydiphenylsulfone compound and the metal salt of phosphate.

Further, rapid increases in consumption of recording sheets due to increasing construction of various networks, and use of facsimiles and copiers have a social problem of waste treatment. As a measure of solving such a problem, a reversible recording material which can be repeatedly recorded and erased is drawing attention.

Reversible recording materials are described in detail in literatures such as the Bulletin of the Pulp and Paper Association 47 11 (1993) p1309–1322. For example, Japanese OPIs 3-230993 and 4-366682 disclose recording materials which utilize a reversible change of the recording material between a transparent state and a white turbid state. In addition, recording materials which use reversibility of a thermochromic substance or a reversible color change of a leuco dye are proposed.

The thermal recording material disclosed in Japanese OPI 4-353490 shows a Macbeth density of ground color of about 0.11 after heating in a dryer at 95° C. for 5 hours, which is a fairly good stability but still insufficient, in term of ground color stability at 120° C.

For the reversible recording materials, one which uses a reversible change of the recording material between a transparent state and a turbid state (in other words, a recording material which utilizes a change in transparency of the recording material) has such disadvantages that: (1) image sharpness is poor, (2) clouding (discoloration) speed is low, and (3) when erasing, temperature control is required. Since this recording material obtains a contrast between transparency and turbidity, there is no problem when it is used in transparent recording sheets such as OHP sheet, but for example, when it is used in opaque recording sheets such as facsimile paper, it is necessary to provide a coloring layer under the coating layer (the layer capable of reversible change between transparent and turbid atates). For this purpose, to provide a contrast in the coating layer, that is, to develop a sharp color of the color layer, the coating layer is desirably a thin layer or, to make the sheet look white, a thicker layer is preferable. Therefore, the thickness of the coating layer must be strictly controlled.

Further, in a reversible recording sheet using a thermochromic material, most thermochromic materials are poor in memorizing properties, and thus require continuous supply of heat to maintain a color developing condition.

On the other hand, as reversible recording sheets which use leuco dyes as chromogenic sources, Japanese OPIs 60-193691 and 60-257289 disclose recording sheets, but these sheets are erased with water or steam, and thus have a problem in practical applications. Japanese OPIs 2-188293 and 2-188294 disclose materials (color developing/erasing agents) which are simple in structure and have both color developing and erasing actions to endow a leuco dye with a reversible change in color by the control of thermal energy.

However, these color developing/erasing agents involve an erasing process already in the color developing process, and are thus low in color developing density. Further, recently, in Japan Hardcopy 1993, Yokota et al. reports a recording sheet which uses an amidophenol derivative having a long-chain alkyl group, but this recording sheet requires temperature control during erasing.

Therefore, a primary object of the present invention is to provide thermal recording sheet which has improved ground color stability to heat and solvents as basic functions. As additional functions, the present invention is to provide a thermal recording sheet which has reversible recording capability enabling recording—erasing —re-recording.

SUMMARY OF THE INVENTION

The above problems are solved by a thermal recording sheet using urea compound, which is quite different from conventional phenolic color developers, as a developer.

Thermal recording sheets using urea compound with phenol type developer (Bisphenol A, Bisphenol S, and so on.) are disclosed in Japanese OPIs 53-140043, 57-87993, 57-82787, and 59-67083. These urea compounds are only limited to the carbon number, and are basically used for depression of melting point of phenoltype developer. Thermal recording sheets using urea compound together phenol type developer have a problem of heat resisitance, and have no recording reversibility.

Patents on monourea compounds for use in thermal recording materials are disclosed in Japanese OPIs 58-211496, 59-184694, and 61-211085. These urea compounds are those in which only the amino group at one side of urea is substituted, and thus basically different from the dimerized and trimerized phenylurea compounds of the present invention.

In general, thermal recording materials are used by dispersing in water, but monourea compounds have a problem since they have a slight solubility in water. Thermal recording materials using these monourea compounds alone have a problem of heat resistance, and have no reversible recording.

The dimerized urea type compounds are disclosed in Japanese OPIs 5-1317152 and 5-147357. These dimerized urea type compounds are characterized by a structure having sulfonyl group adjacent to the urea structure (Ar—SO$_2$—NH—C(=O)—NH—). However, the thermal recording sheets using these dimerized urea also have a problem in heat resistance, and have no reversible recording.

In accordance with the present invention, there is provided in a thermal recording sheet having a thermal recording layer containing a colorless or pale colored dye precursor and a color developer reactable with the dye precursor upon heating to develop a color, characterized in that the color developer is a urea compound having at least two groups of Formula (1) (hereinafter referred to as "phenylurea structure") in the molecule, and the thermal recording layer contains at least one of the urea compound.

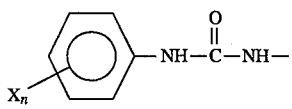

(1)

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group.

As the urea compound used in the present invention having at least two groups of Formula (1) in the molecule, those of Formula (2), (3), or (4) are practically preferable. In other words, it is preferable that in the thermal recording sheet having a thermal recording layer containing a colorless or pale colored dye precursor and a color developer which reacts with the dye precursor upon heating to develop a color, the color developer is a urea compound of Formula (2), (3), or (4), and the thermal recording layer contains at least one of the urea compounds.

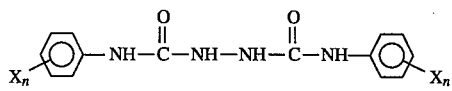

(2)

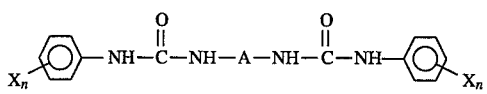

(3)

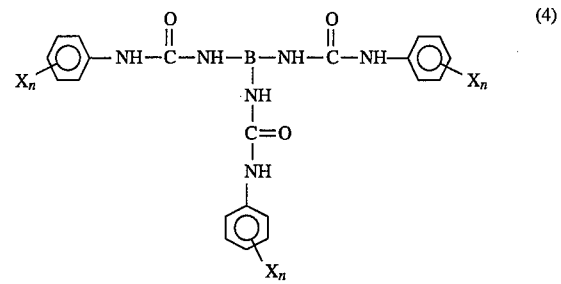

(4)

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group. A denotes a divalent group comprising 30 or less carbon atoms, and B denotes a trivalent group comprising 30 or less carbon atoms.

The urea compound of Formula (2), (3), or (4) is a compound having two or three phenylurea structures of Formula (1). The urea compound of Formula (2) is a compound in which two phenylurea structures are directly bonded, and the urea compound of Formula (3) or (4) is a compound in which two or three phenylurea structures are bonded through a joint group. The joint group is a divalent or trivalent group comprising 30 or less carbon atoms.

The urea compound of Formula (2) or (3) (hereinafter referred to as "dimerized urea compound") and the urea compound of Formula (4) (hereinafter referred to as "trimerized urea compound") can be individually synthesized, for example, by a reaction of amines with an isocyanate compound.

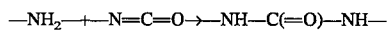

First, the dimerized urea compound of Formula (3) can be synthesized (a) by reacting diamines with a monoisocyanate compound, or (b) by reacting a diisocyanate compound with monoamines.

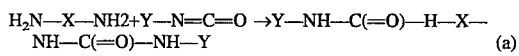  (a)

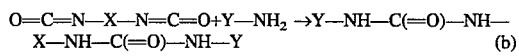  (b)

When diamines are reacted with a monoisocyanate compound, the diamines include carbohydrazide, ethylenediamine, 1,2-propanediamine, 1,3-propanediamine, 1,4-diaminobutane, 1,3-diaminopentane, 1,5-diaminopentane, 1,6-diaminohexane, 1,7-diaminoheptane, 1,8-diaminooctane, 1,9-diaminononane, 1,10-diaminodecane, 1,11-diaminoundecane, 1,12-diaminododecane, 1,2-diamino-2-methylpropane, 1,3-diamino-2,2-dimethylpropane, 1,5-diamino-2-methylpentane, 1,5-diamino-2,2-dimethylpentane, trimethylhexamethylenediamine, diethylenetriamine, triethylenetetramine, tetraethylenepentamine, 3,3'-diaminodipropylamine, N,N-bis(3-aminopropyl)methylamine, bis(3-aminopropyl) ether, 1,8-diamino-3,6-dioxaoctane, ethyleneglycolbis(3-aminopropyl)ether, 1,2-diaminocyclohexane, 1,3-diaminocyclohexane, 1,4-diaminocyclohexane, 1,3-di(aminomethyl)cyclohexane, 1,4-di(aminomethyl)cyclohexane, 4,4'-diaminodiphenylsulfone, 3,3'-diaminodiphenylsulfone, 4,4'-diaminodiphenylsulfide, 4,4'-diaminodiphenylether, 3,4'-diaminodiphenylether, 4,4'-diaminodiphenylether, 3,4'-diaminodiphenylether, 4,4'-diaminodicyclohexylmethane, 4,4'-diaminodiphenylmethane, 3,3'-diaminodiphenylmethane, 4,4'-diamino-3,3'-dichlorodiphenylmethane, 4,4'-diamino-1,2-diphenylethane, 4,4'-diamino-2,2'-dimethylbiphenyl, 4,4'-diaminodiphenylamine, 2,2'-diaminodiphenyldisulfide, 4,4'-diaminodiphenyldisulfide, 1,3-bis(m-aminophenoxy)benzene, 1,4-bis(m-aminophenoxy)benzene, 2,2-bis(4-aminophenxyphenyl)propane, 2,2-bis[4-(4-aminophenoxy)phenyl]hexafluoropropane, a,a'-bis(4-aminophenyl)-1,4-diisopropylbenzen 3,3'-diaminobenzophenone, 4,4'-diaminobenzophenone, 2,4-diaminoazobenzene, 4,4'-diaminostilbene, 4,4'-diaminostilbene-2,2'-disulfonic acid, o-phenylenediamine, m-phenylenediamine, p-phenylenediamine, 4-chloro-o-phenylenediamine, 5-chloro-m-phenylenediamine, 2-chloro-p-phenylenediamine, 2-nitro-1,4-phenylenediamine, 4-nitro-1,2-phenylenediamine, 4-nitro-1,3-phenylenediamine, 2,4-diaminoanisole, p,p'-methylenedianiline, m-xylylenediamine, p-xylylenediamine, 2,4-diaminotoluene, 2,6-diaminotoluene, 3,4-diaminobenzoic acid, 3,5-diaminobenzoic acid, 1,5-diaminonaphthalene, 1,8-diaminonaphthalene, 2,3-dianononaphthalene, 1,2-diaminoanthraquinone, 1,4-diaminoanthraquinone, 1,5-diaminoanthraquinone, 2,6-diaminoanthraquinone, 1,4-diamino-2,3-dicyano-9.10-anthraquinone, 2,3-diaminopyridine, 2,6-diaminopyridine, 3,4-diaminopyridine, 2,4-diamino-6-chloropyrimidine, 2,4-diamino-6-phenyl-1,3,5-triazine, 9,9-bis(4-aminophenyl)fluorene, piperazine, N-aminoethylpiperazine, 1,4-bid(3-aminopropyl)piperazine, and isophoronediamine; the monoisocyanate compound includes aromatic isocyanate compounds such as phenylisocyanate, o-tolylisocyanate, m-tolylisocyanate, p-tolylisocyanate, 3,4-dimethylphenylisocyanate, 2,6-dimethylphenylisocyanate, 3,4,5-trimethyl phenylisocyanate, o-trifluoromethylphenylisocyanate, m-trifluoromethylphenylisocyanate, p-trifluoromethylphenylisocyanate, 2-methoxyphenylisocyanate, 3-methoxyphenylisocyanate, 4-methoxyphenylisocyanate, p-bromophenylisocyanate, o-fluorophenylisocyanate, m-fluorophenylisocyanate, p-fluorophenylisocyanate, o-chlorophenylisocyanate, 2,5-dichlorophenylisocyanate, 3,4-dichlorophenylisocyanate, 2,6-dichlorophenylisocyanate, o-nitrophenylisocyanate, m-nitrophenylisocyanate, pnitrophenylisocyanate, p-dimethylaminophenylisocyanate, and p-diethylaminophenylisocyanate, and any combinations of both compounds can be used.

On the other hand, when a diisocyanate compound is reacted with monoamines, the diisocyanate compound includes 2,4-toluenediisocyanate (2,4-TDI), 2,6-toluenediisocyanate (2,6-TDI), 4,4'-diphenylmethanediisocyanate (MDI), 1,5-naphthalenediisocyanate (NDI), tolidinediisocyanate (TODI), hexamethylenediisocyanate (HDI), isophoronediisocyanate (IPDI), p-phenylenediisocyanate, m-phenylenediisocyanate, trans-cyclohexane-1,4-diisocyanate, xylylenediisocyanate (XDI), 4,4'-dicyclohexylmethanediisocyanate (hydrogenated MDI), lysinediisocyanate (LDI), m-tetramethylxylene diisocyanate (m-TMXDI), and p-tetramethylxylenediisocyanate (p-TMXDI); the monoamines include aromatic amines such as aniline, o-toluidine, m-toluidine, p-toluidine, o-ethylaniline, m-ethylaniline, p-ethylaniline, p-n-propylaniline, p-iso-propylaniline, p-n-butylaniline, 2-sec-butylaniline, 4-sec-butylaniline, 4-tert-butylaniline, p-n-amylaniline, p-n-hexylaniline, p-n-heptylaniline, p-n-octylaniline, p-n-nonylaniline, p-n-decylaniline, p-undecylaniline, p-dodecylaniline, 2,3-xylidine, 2,4-xylidine, 2,5-xylidine, 8,4-xylidine, mesitylamine, 2,6-diethylaniline, o-aminobenzotrifluoride, m-aminobenzotriluoride, p-aminobenzotrifluoride, o-methoxyaniline, m-methoxyaniline, p-methoxyaniline, o-ethoxyaniline, m-ethoxyaniline, p-ethoxyaniline, 4-tert-butoxyaniline, 2,4-dimethoxyaniline, 2,5-dimethoxyaniline, 3,4-dimethoxyaniline, 3,5-dimethoxyaniline, o-chloroaniline, m-chloroaniline, p-chloroaniline, o-bromoaniline, m-bromoaniline, p-bromoaniline, o-fluoroaniline, m-fluoroaniline, p-fluoroaniline, 2,3-dichloroaniline, 2,4-dichloroaniline, 2,5-dichloroaniline, 2,6-dichloroaniline, 3,4-dichloroaniline, 3,5-dichloroaniline, 2,4-dibromoaniline, 2,5-dibromoaniline, 2,6-dibromoaniline, 2,4-difluoroaniline, 2,5-difloroaniline, 2,6-difluoroaniline, 3,4-difluoroaniline, 2,3,4-trichloroaniline, 2,4,5-trichloroaniline, 2,4,6-trichloroaniline, o-nitroaniline, m-nitroaniline, p-nitroaniline, o-cyanoaniline, m-cyanoaniline, p-cyanoaniline, methyl o-aminobenzoate, methyl m-aminobenzoate, methyl p-aminobenzoate, ethyl o-aminobenzoate, ethyl m-aminobenzoate, ethyl p-aminobenzoate, n-propyl p-aminobenzoate, iso-propyl p-aminobenzoate, n-butyl p-aminobenzoate, iso-butyl p-aminobenzoate, phenyl o-aminobenzoate, phenyl m-aminobenzoate, phenyl p-aminobenzoate, benzyl o-aminobenzoate, benzyl m-aminobenzoate, benzyl p-aminobenzoate, p-nitrophenyl o-aminobenzoate, 2-diethylaminoethyl p-aminobenzoate, 2'-aminoacetophenone, 3'-aminoacetophenone, 4'-aminoacetophenone, 2-aminobenzophenone, 3-aminobenzophenone, 4-aminobenzophenone, m-aminobenzoylmethylamide, 2-aminodiphenylether, 3-aminodiphenylether, 4-aminodiphenylether, 2-amino-4'-chlorodiphenylether, 4-amino-4'-chlorodiphenylether, 4-amino-4'-aminodiphenylmethane, 4-amino-4'-chlorodiphenylmethane, 2-amino-5-chlorotoluene, 4-amino-2-chlorotoluene, 2-amino-5-boromobenzotrifluoride, 2-amino-5-chlorobenzotrifluoride, 3-amino-4-chlorobenzotrifluoride, 5-amino-2-chlorobenzotrifluoride, and any combinations of both compounds can be used.

The dimerized urea compound of Formula (2) can be synthesized using hydrazine as the diamine and the above compounds as the monoisocyanate compound. On the other hand, the trimerized urea compound of Formula (4) can be synthesized by a method of reacting triamines with a mofioisocyanate compound or a method of reacting a triisocyanate compound with monoamines.

First, when triamines are reacted with a monoisocyanate compound, the triamines can be 1,2,4-triaminobenzene, tris(2-aminoethyl)amine, melamine, 2,4,6-triaminopyrimidine, and triamtherene, the monoisocyanate compound can be the above described compounds, and any combinations of both compounds can be used. When a triisocyanate compound is reacted with monoamines, the triisocyanate compound can be triphenylmethanetriisocyanate, tris(isocyanatephenyl)thiophosphate, lysine ester triisocyanate, 1,6,11-undecanetriisocyanate, 1,8-diisocyanate-4-isocyanatemethyloctane, 1,3,6-hexamethylenetriisocyanate, and bicycloheptanetriisocyanate; the monoamines can be the above described compounds, and any combinations of both compounds can be used.

Practical examples of the urea compound of Formula (2), (3), or (4) are shown below:

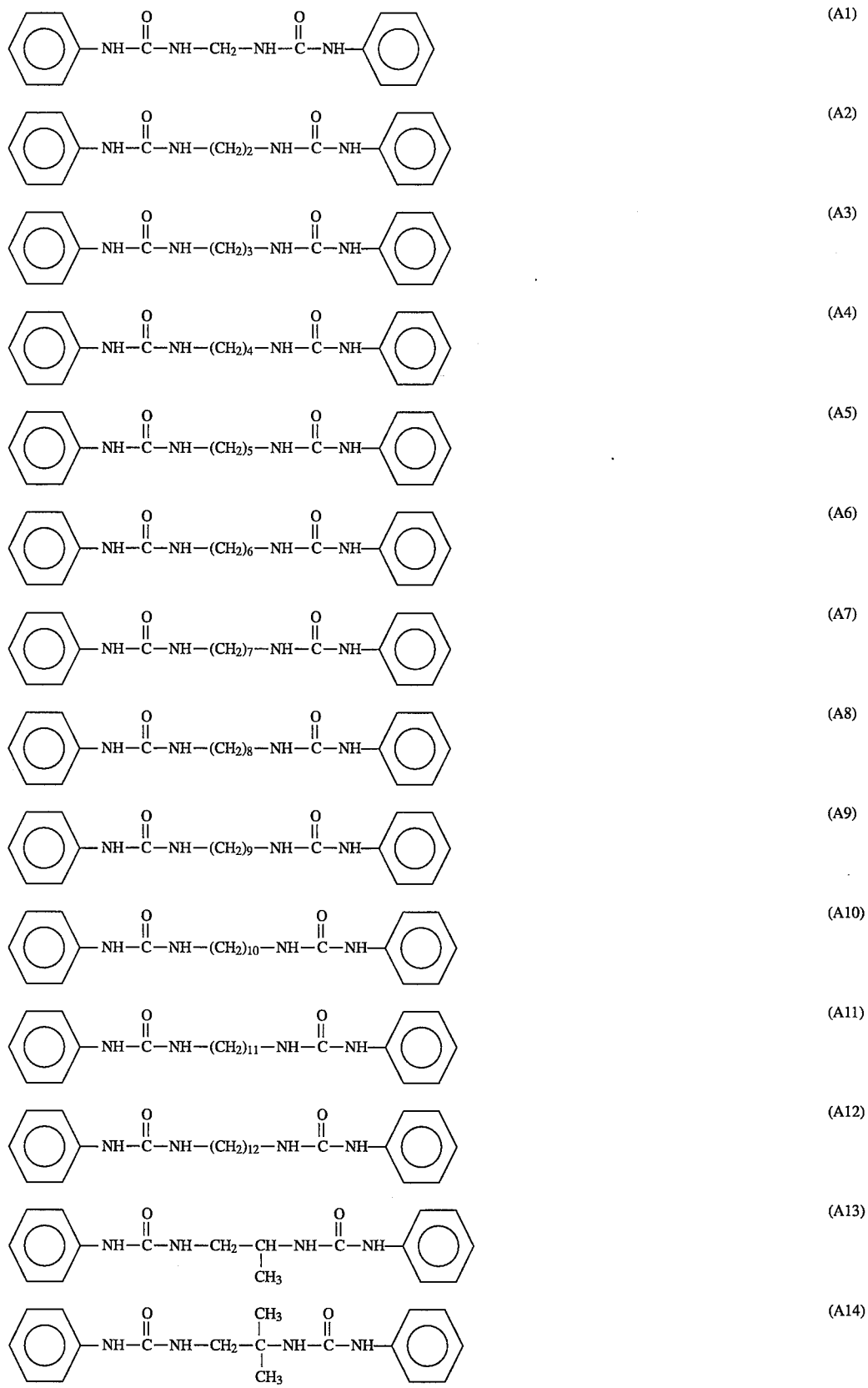

-continued
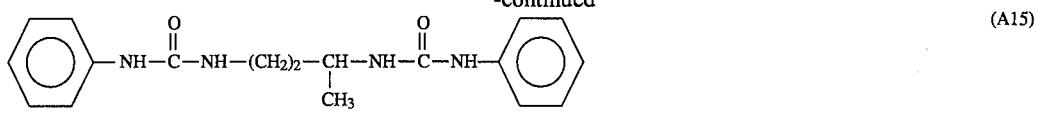 (A15)
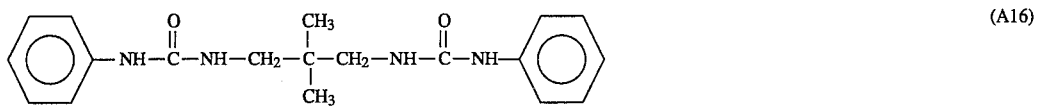 (A16)
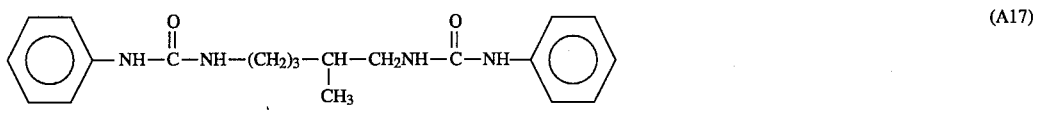 (A17)
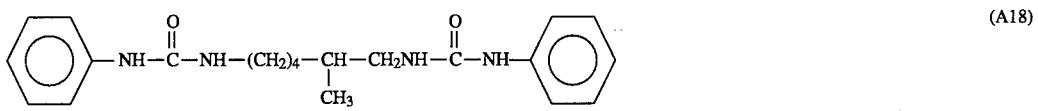 (A18)
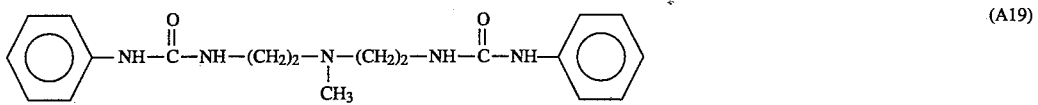 (A19)
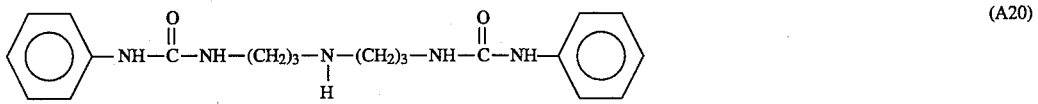 (A20)
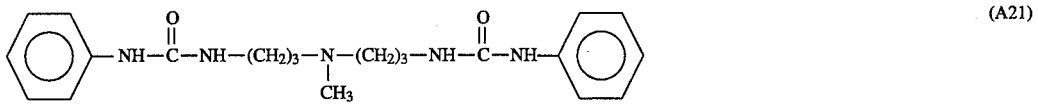 (A21)
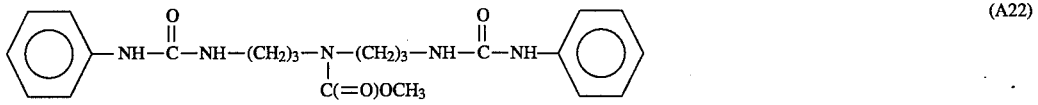 (A22)
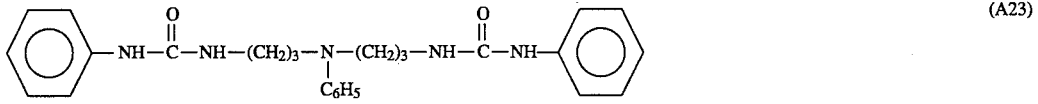 (A23)
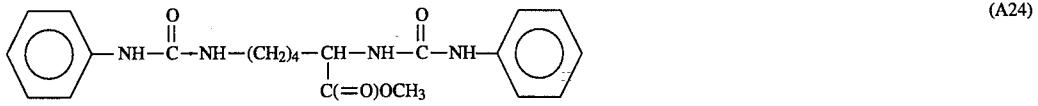 (A24)
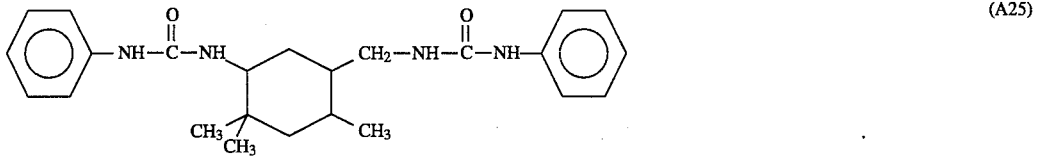 (A25)
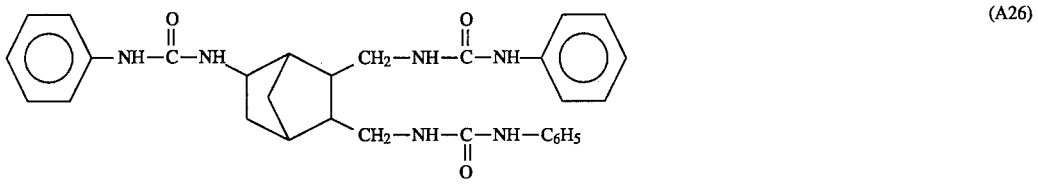 (A26)

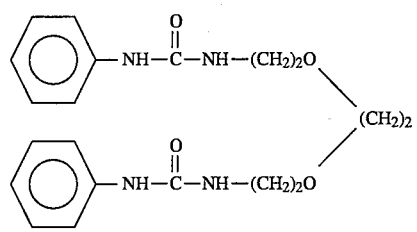 (A27)
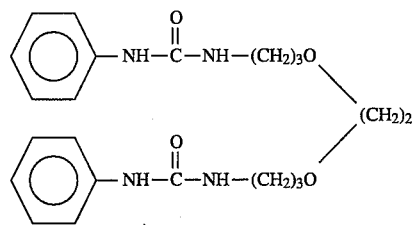 (A28)
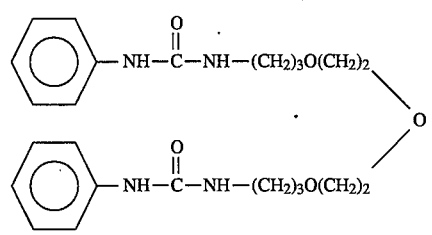 (A29)
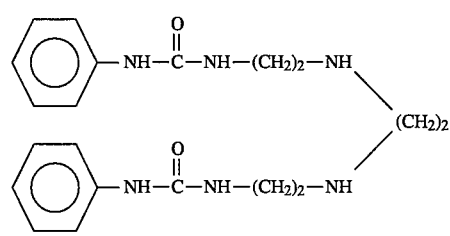 (A30)
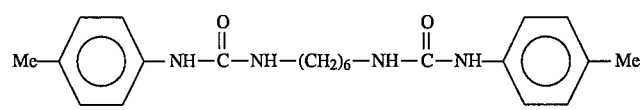 (A31)
Me = -Methyl
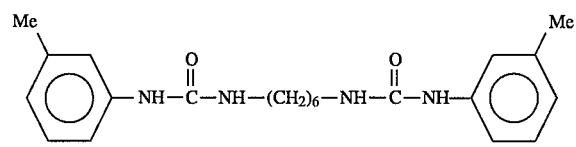 (A32)
Me = -Methyl
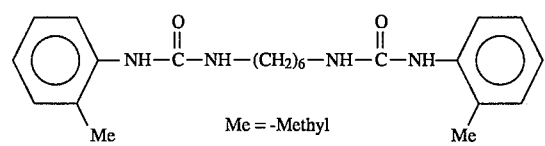 (A33)
Me = -Methyl
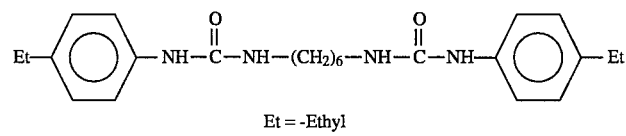 (A34)
Et = -Ethyl
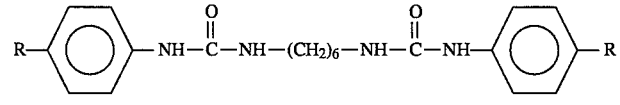 (A35)
R = -sec-Butyl -continued
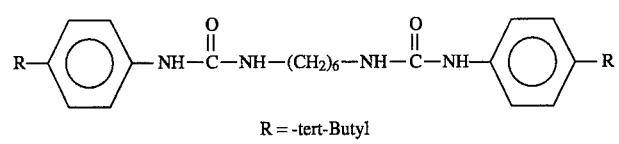
R = -tert-Butyl
(A36)
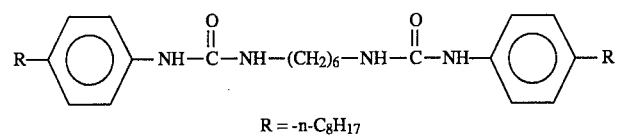
R = -n-C$_8$H$_{17}$
(A37)
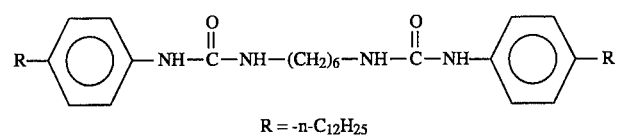
R = -n-C$_{12}$H$_{25}$
(A38)
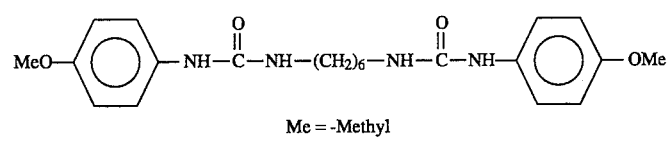
Me = -Methyl
(A39)
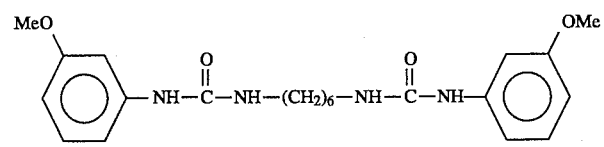
Me = -Methyl
(A40)
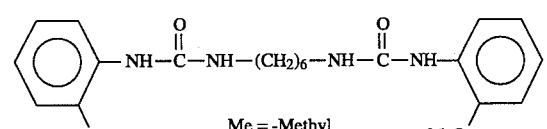
Me = -Methyl
(A41)
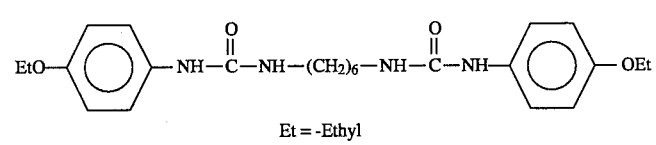
Et = -Ethyl
(A42)
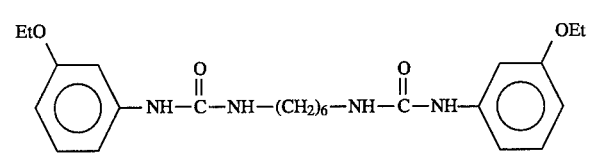
Et = -Ethyl
(A43)
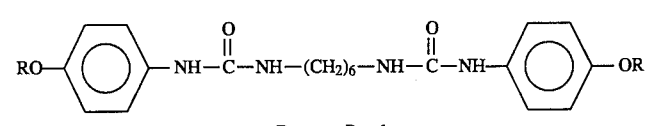
R = -tert-Butyl
(A44)
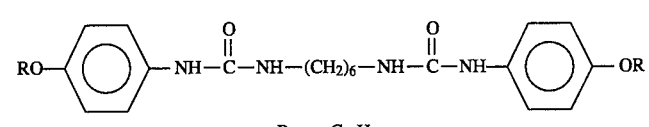
R = -n-C$_{10}$H$_{21}$
(A45)
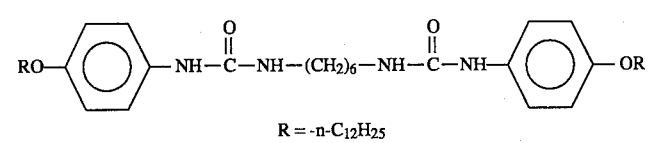
R = -n-C$_{12}$H$_{25}$
(A46)

-continued
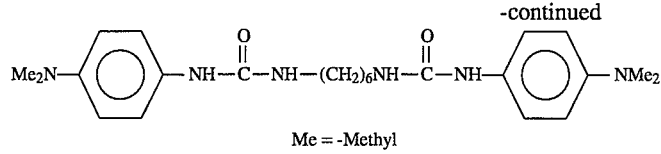  (A47)
Me = -Methyl
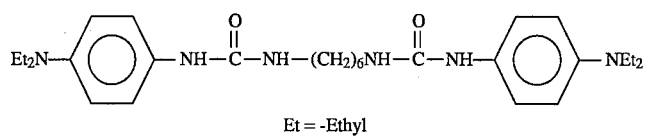  (A48)
Et = -Ethyl
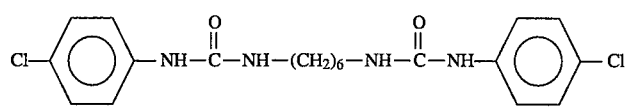  (A49)
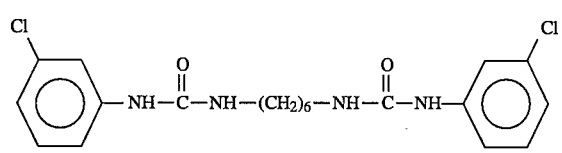  (A50)
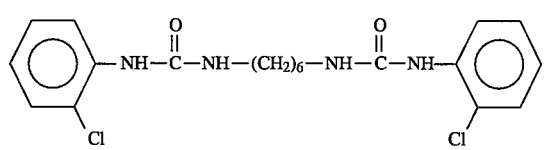  (A51)
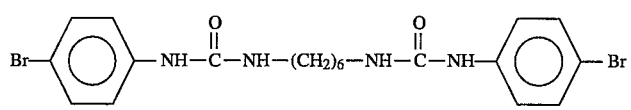  (A52)
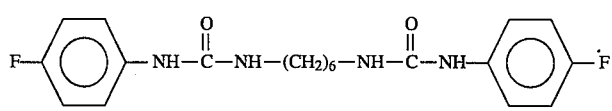  (A53)
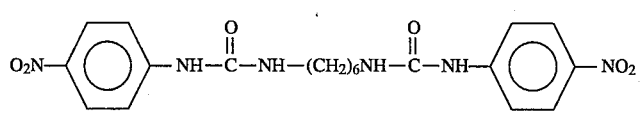  (A54)
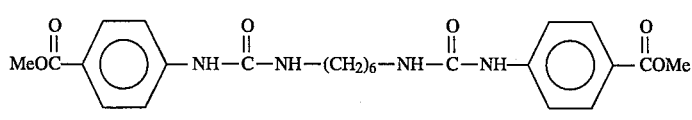  (A55)
Me = -Methyl
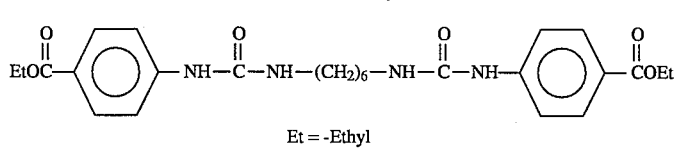  (A56)
Et = -Ethyl
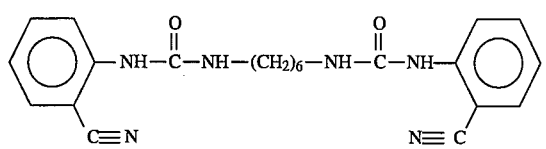  (A57)
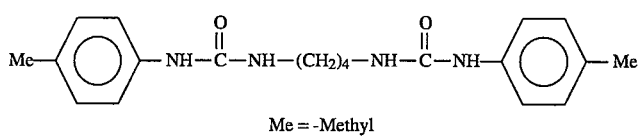  (A58)
Me = -Methyl

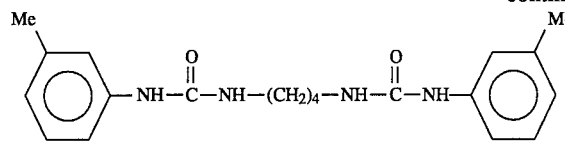
(A59)
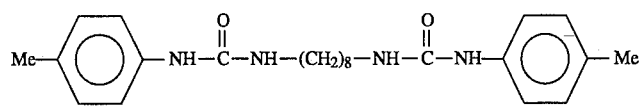
(A60)
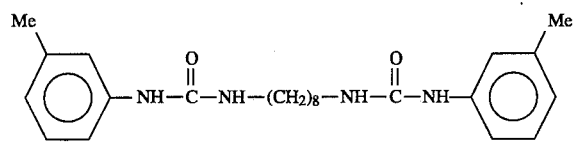
(A61)
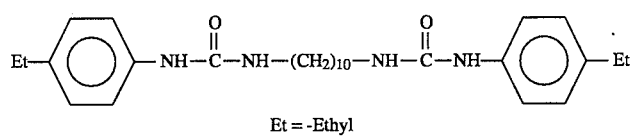
(A62)
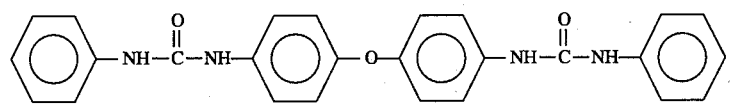
(A63)
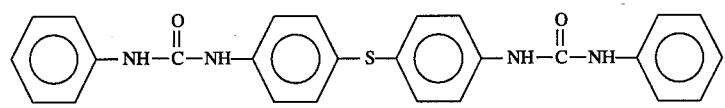
(A64)
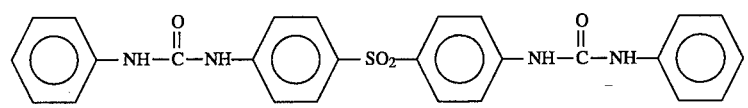
(A65)
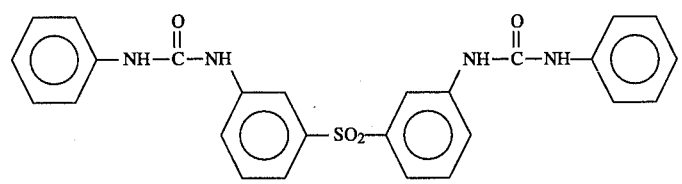
(A66)
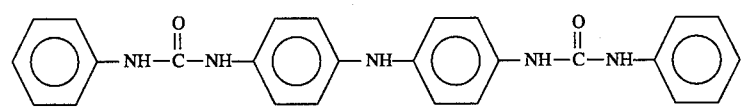
(A67)
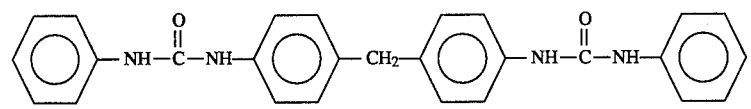
(A68)
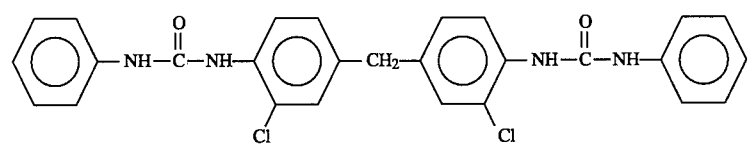
(A69)

-continued
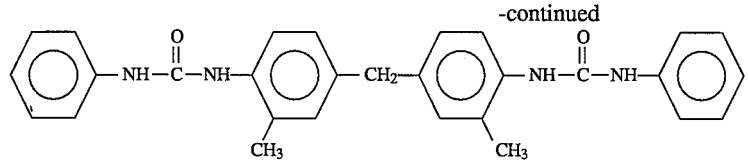 (A70)
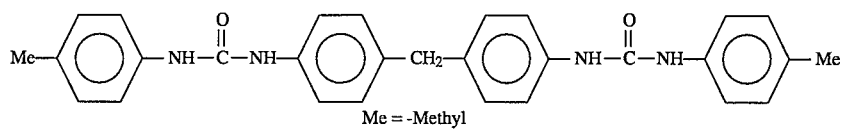 (A71)
Me = -Methyl
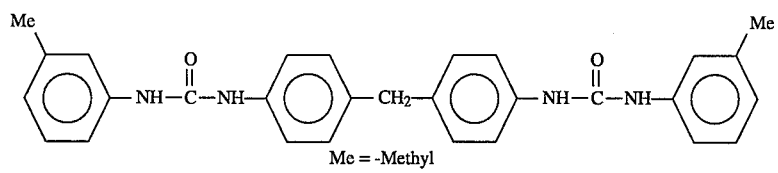 (A72)
Me = -Methyl
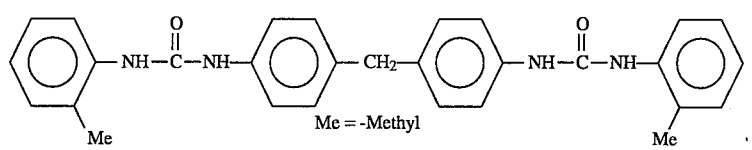 (A73)
Me = -Methyl
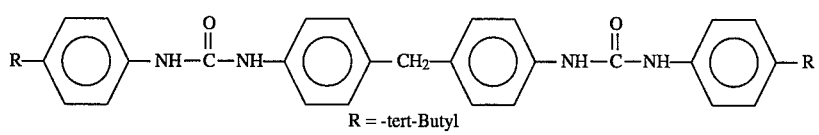 (A74)
R = -tert-Butyl
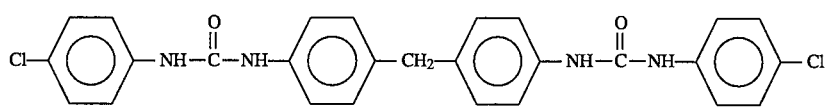 (A75)
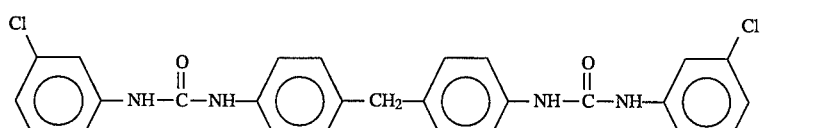 (A76)
 (A77)
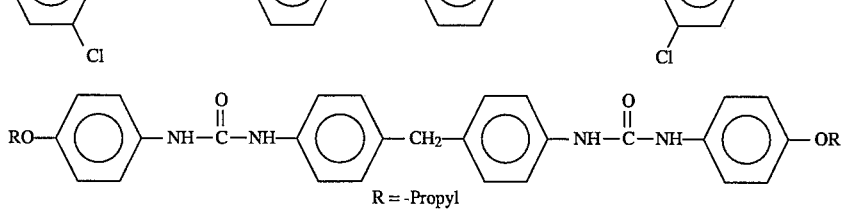 (A78)
R = -Propyl
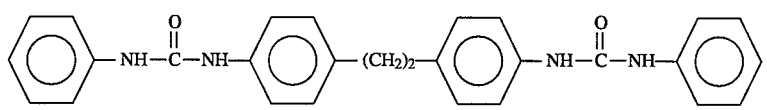 (A79)
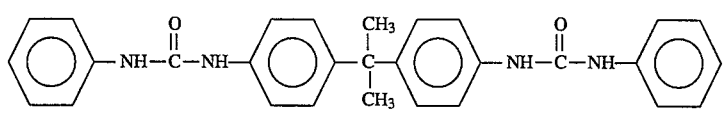 (A80)
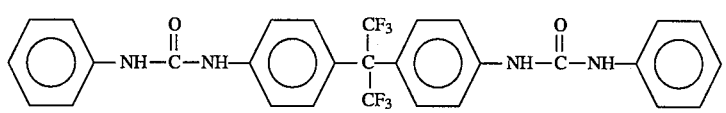 (A81)

-continued
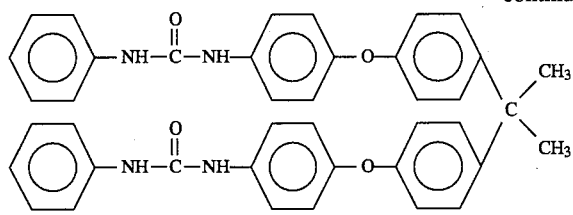 (A82)
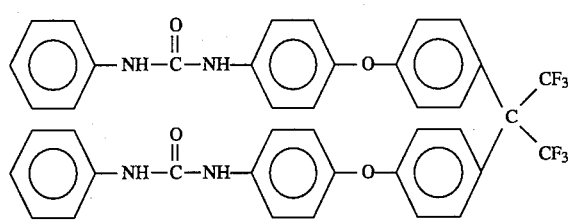 (A83)
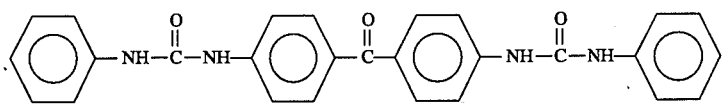 (A84)
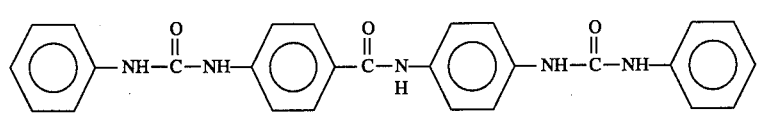 (A85)
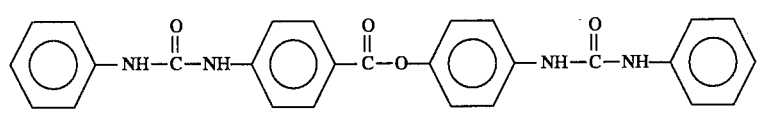 (A86)
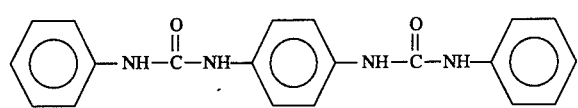 (A87)
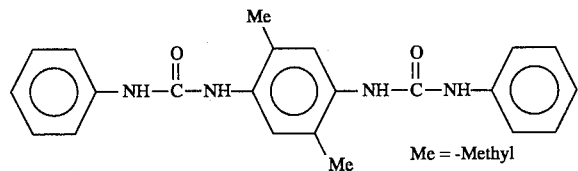 (A88)
Me = -Methyl
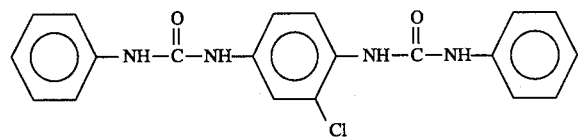 (A89)
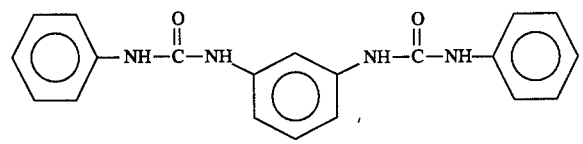 (A90)
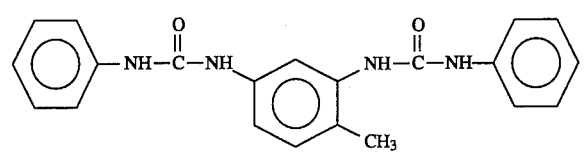 (A91)

-continued
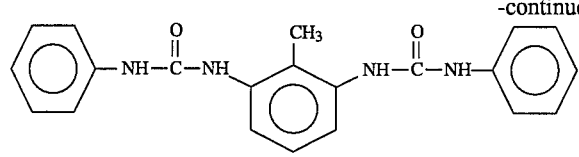 (A92)
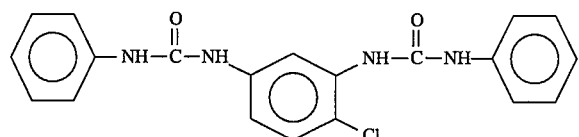 (A93)
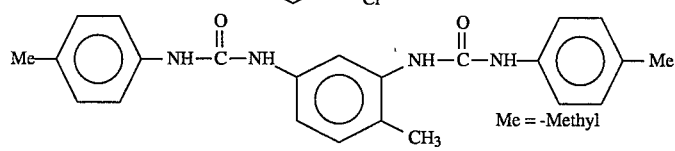 (A94)
Me = -Methyl
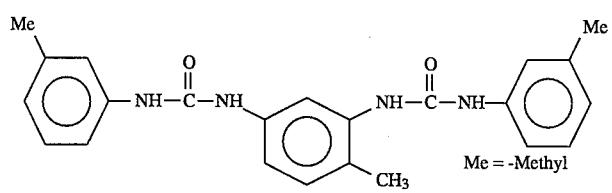 (A95)
Me = -Methyl
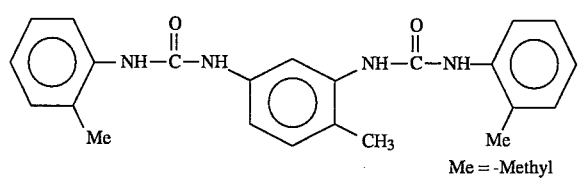 (A96)
Me = -Methyl
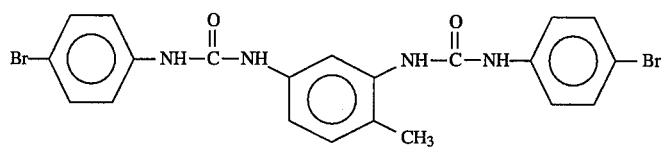 (A97)
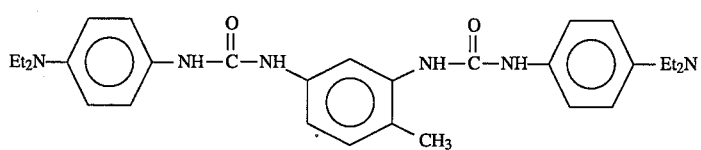 (A98)
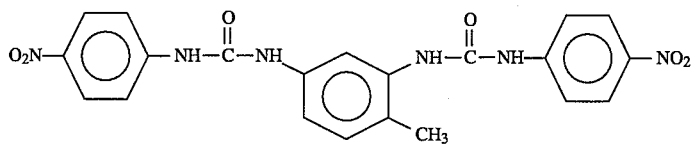 (A99)
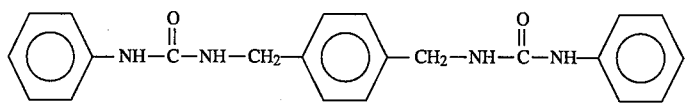 (A100)
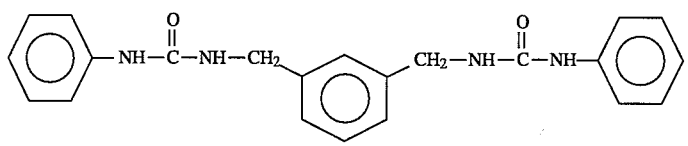 (A101)

-continued
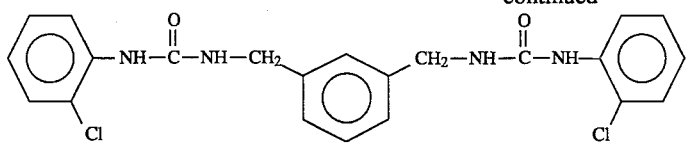 (A102)
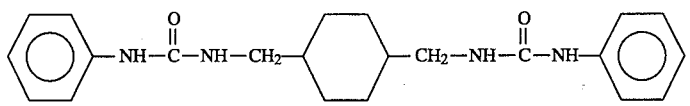 (A103)
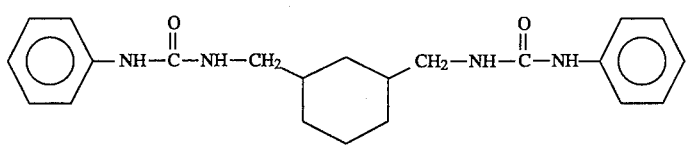 (A104)
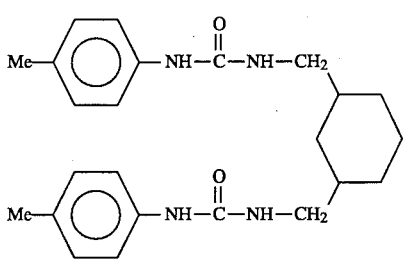 (A105)
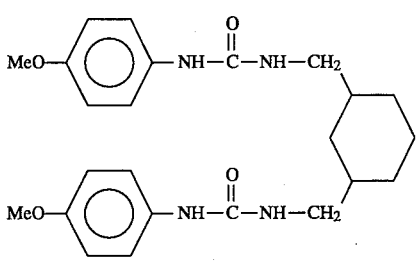 (A106)
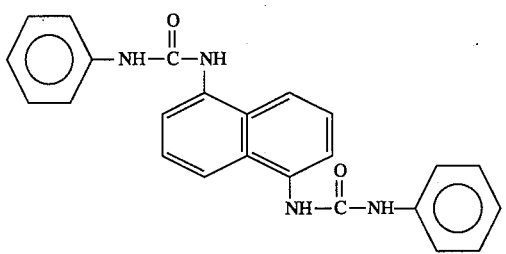 (A107)
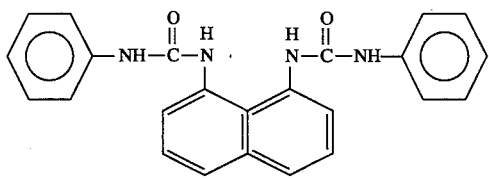 (A108)
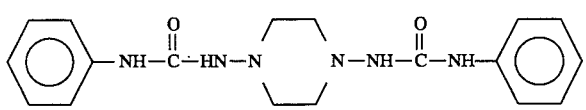 (A109)
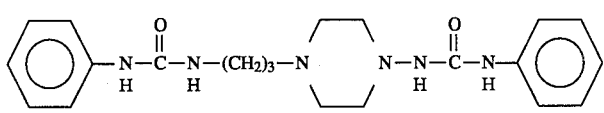 (A110)

-continued
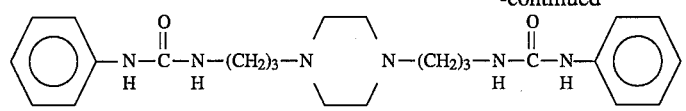 (A111)
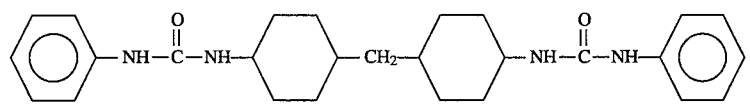 (A112)
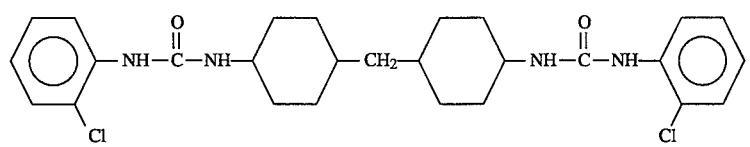 (A113)
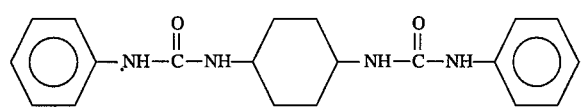 (A114)
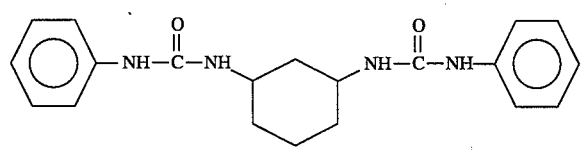 (A115)
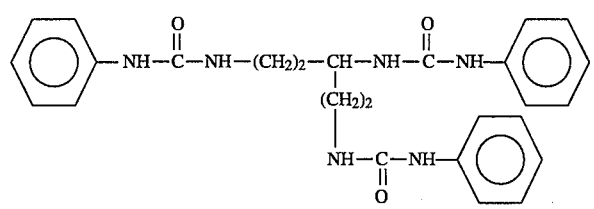 (A116)
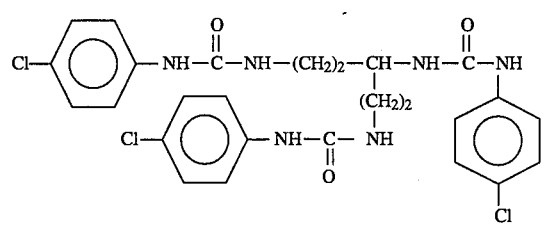 (A117)
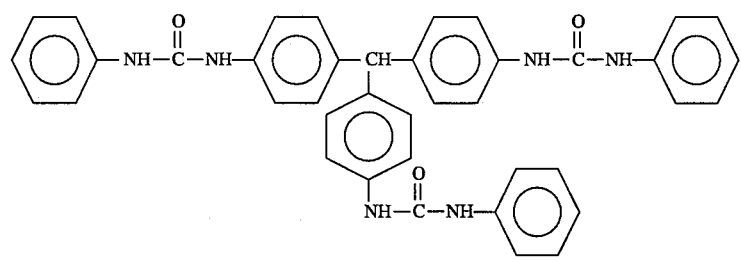 (A118)
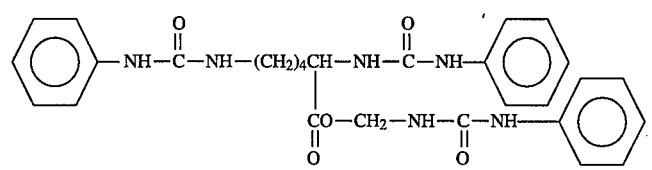 (A119)
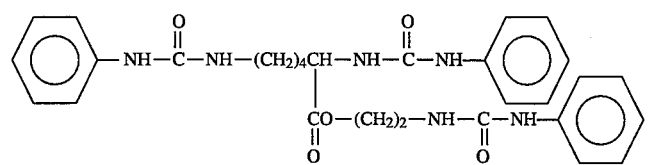 (A120)

-continued
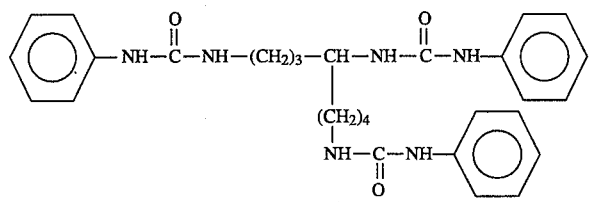 (A121)
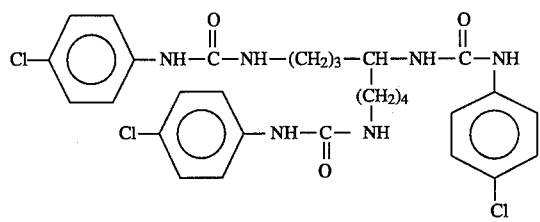 (A122)
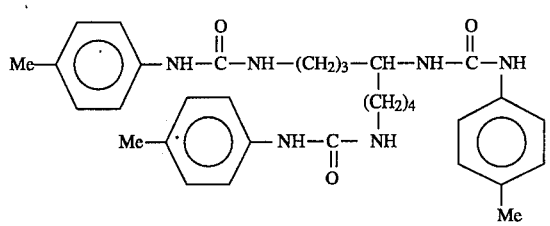 (A123)
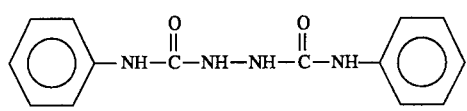 (A124)
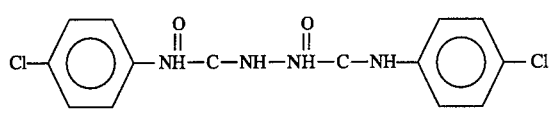 (A125)
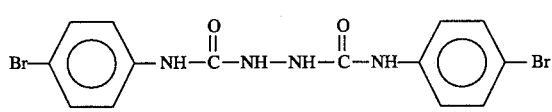 (A126)
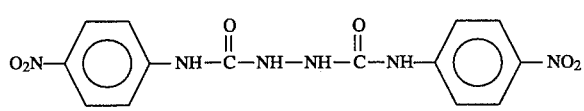 (A127)
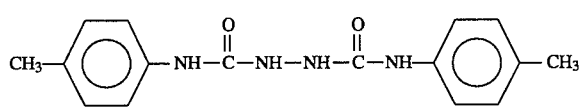 (A128)
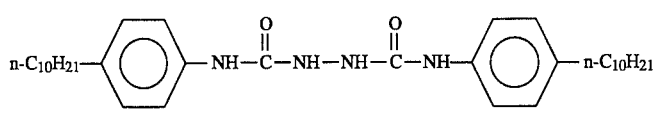 (A129)
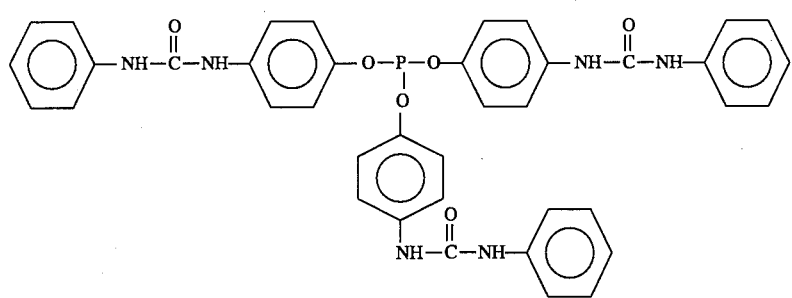 (A130)

-continued
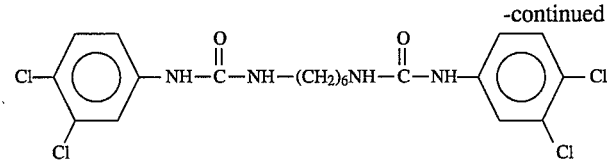 (A131)
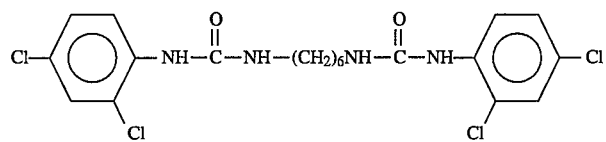 (A132)
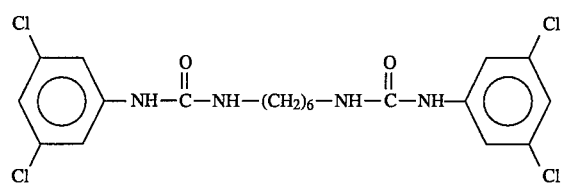 (A133)
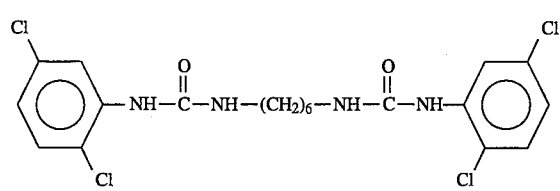 (A134)
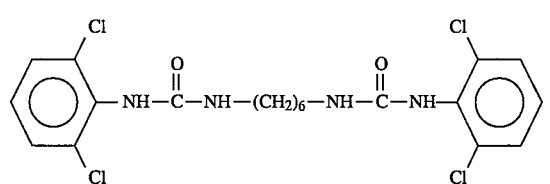 (A135)
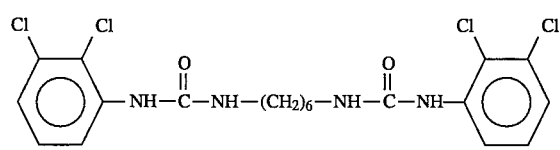 (A136)
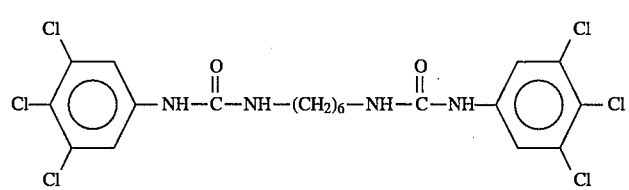 (A137)
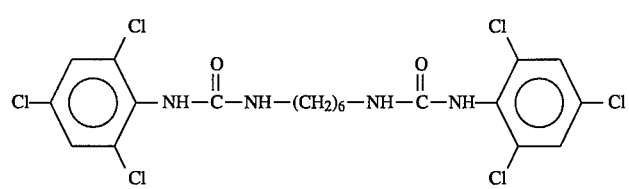 (A138)
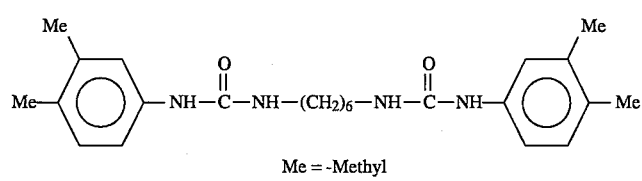 (A139)
Me = -Methyl -continued
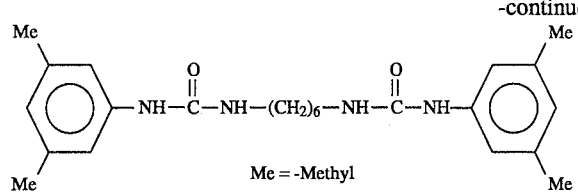 (A140)
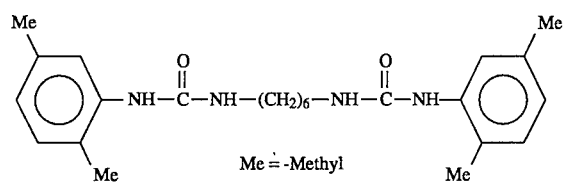 (A141)
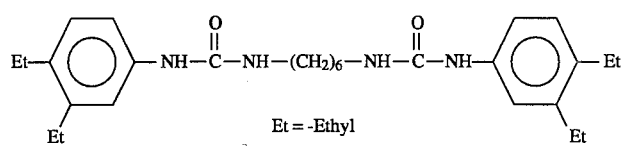 (A142)
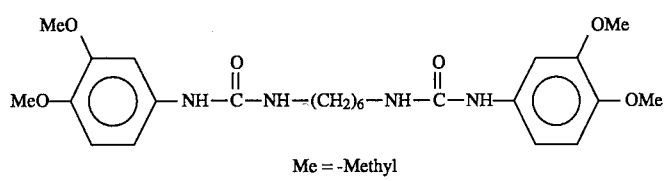 (A143)
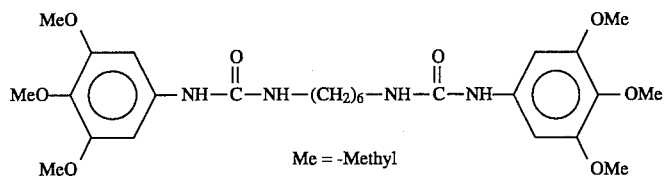 (A144)
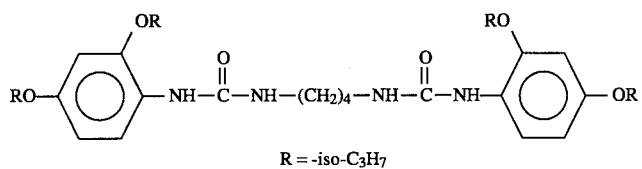 (A145)
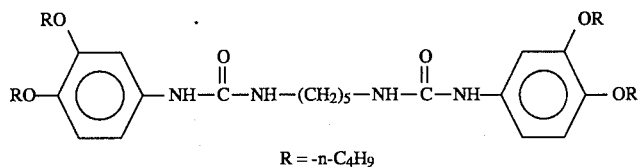 (A146)
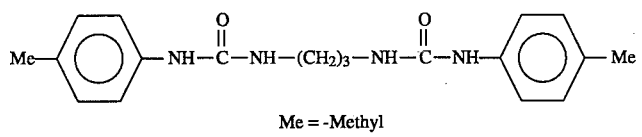 (A147)
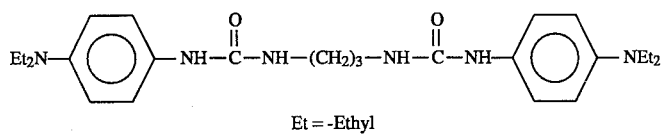 (A148)
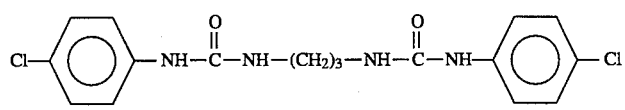 (A149)

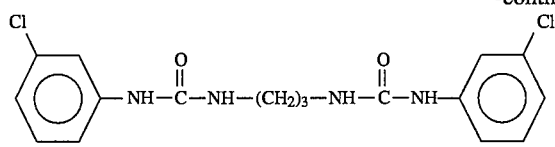 (A150)
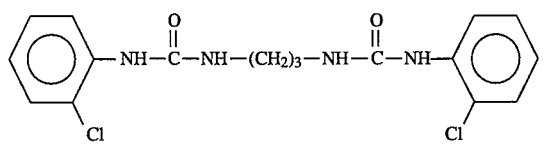 (A151)
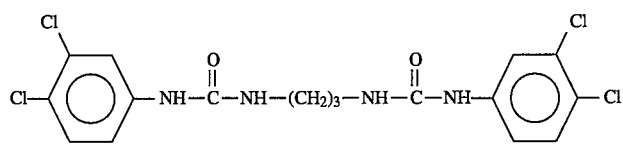 (A152)
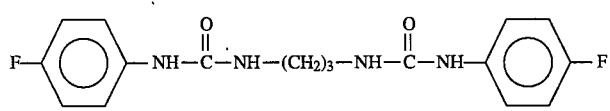 (A153)
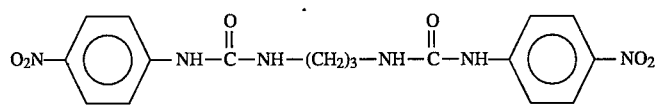 (A154)
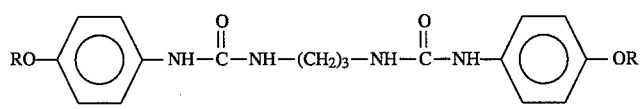 (A155)
R = -tert-$C_4H_9$
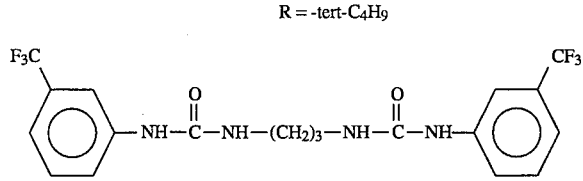 (A156)
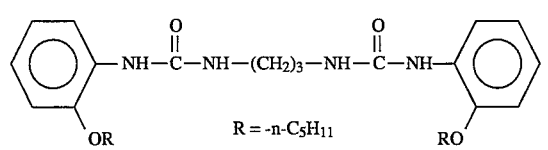 (A157)
R = -n-$C_5H_{11}$
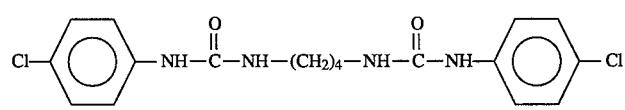 (A158)
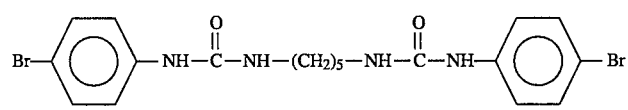 (A159)
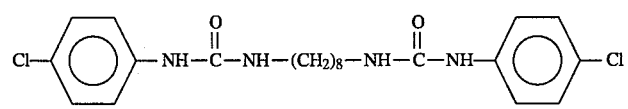 (A160)
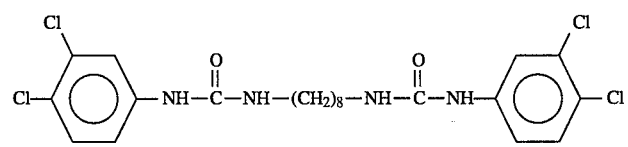 (A161)

-continued
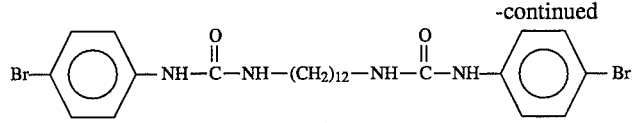 (A162)
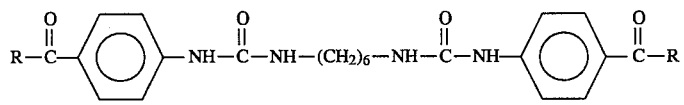 (A163)
Me = -Methyl
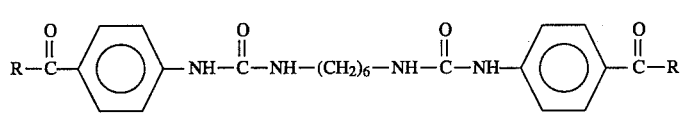 (A164)
Me = -Phenyl
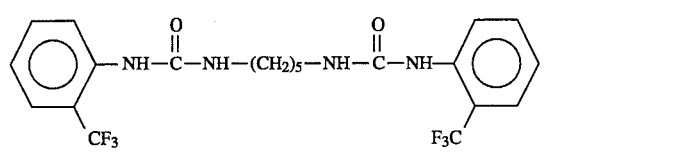 (A165)
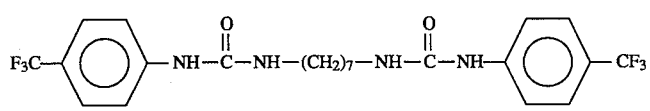 (A166)
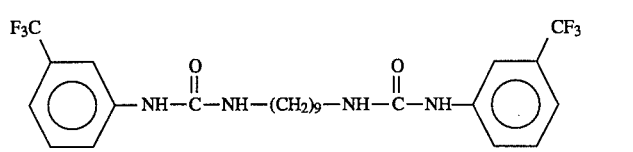 (A167)
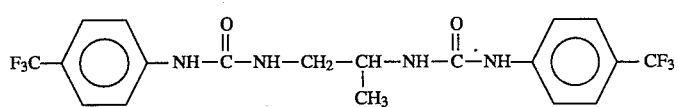 (A168)
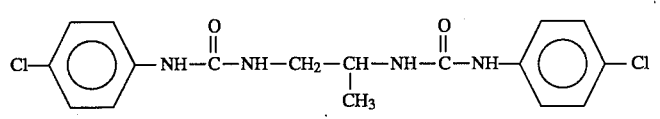 (A169)
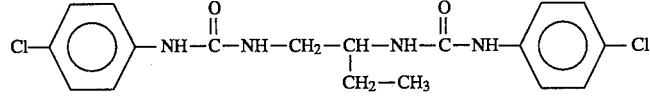 (A170)
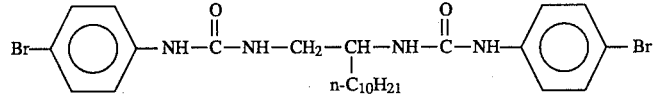 (A171)
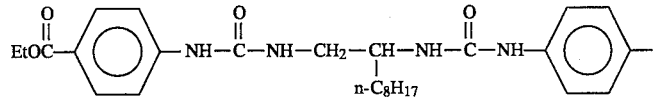 (A172)
Et = -Ethyl
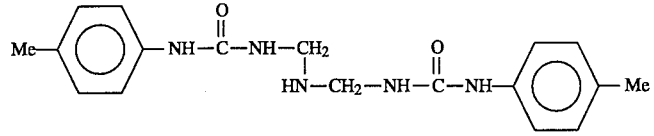 (A173)

-continued
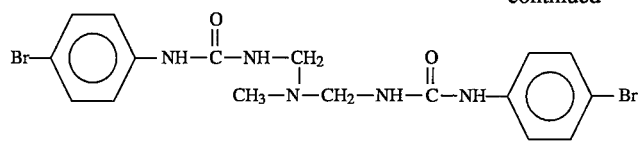 (A174)
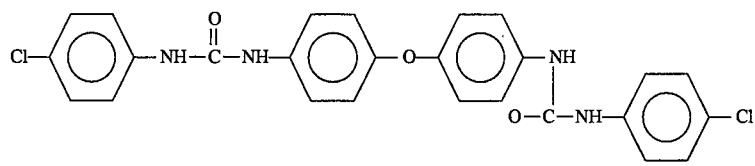 (A175)
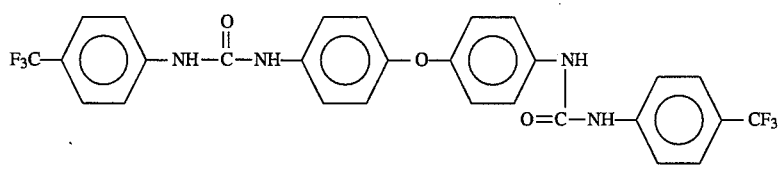 (A176)
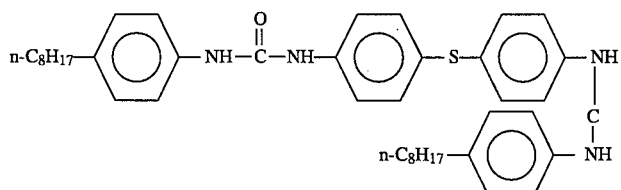 (A177)
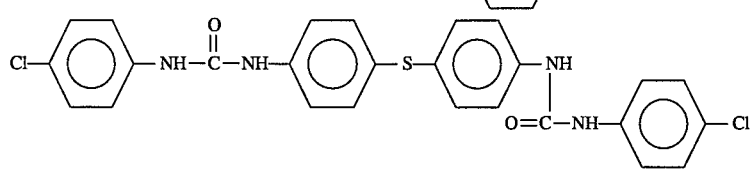 (A178)
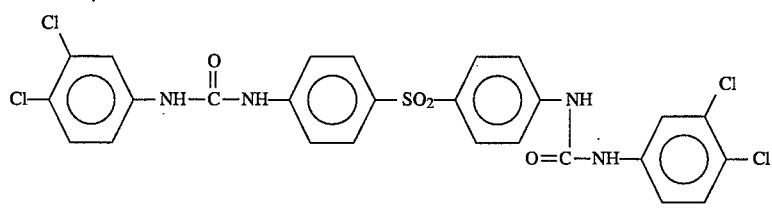 (A179)
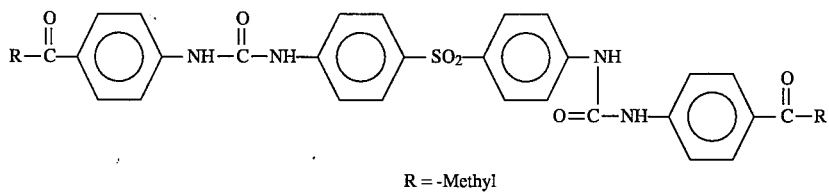 (A180)
R = -Methyl
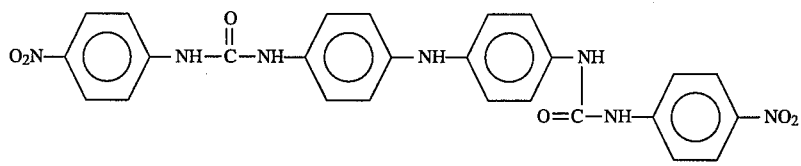 (A181)
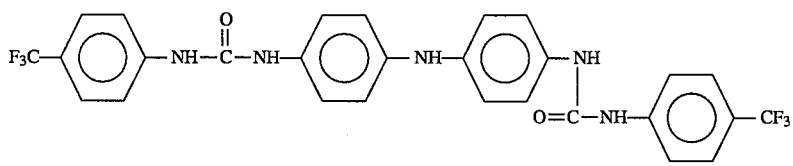 (A182)

-continued
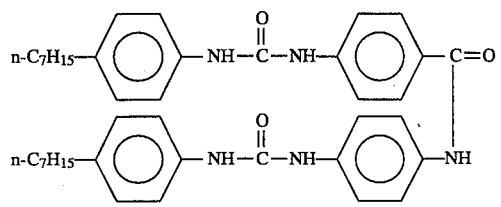
(A183)
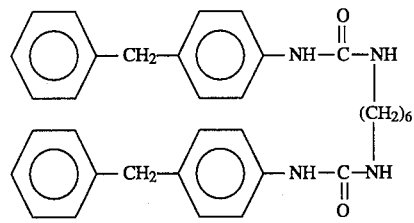
(A184)
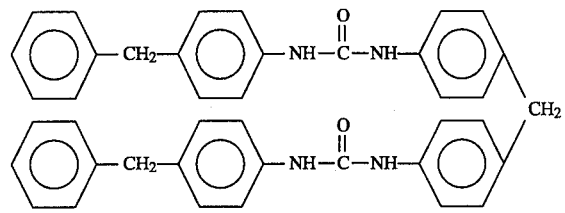
(A185)
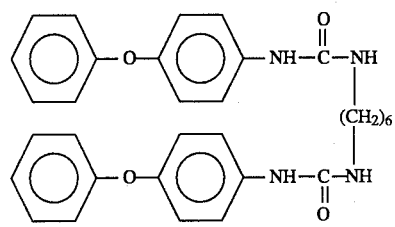
(A186)
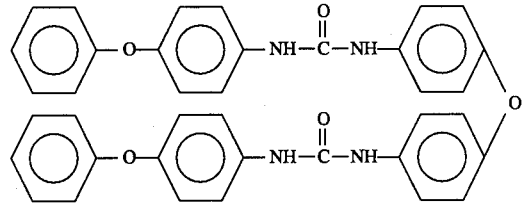
(A187)
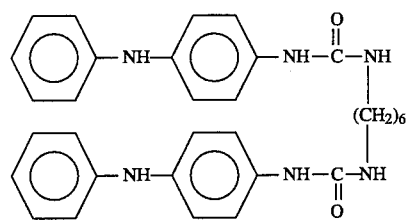
(A188)
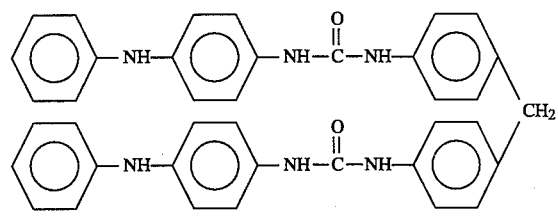
(A189)

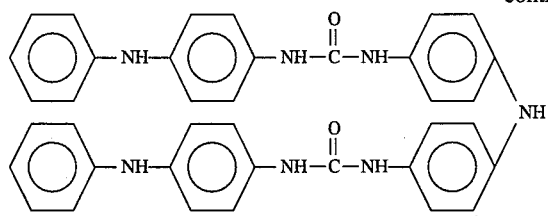 (A190)
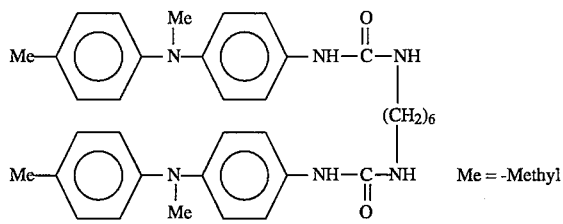 (A191)
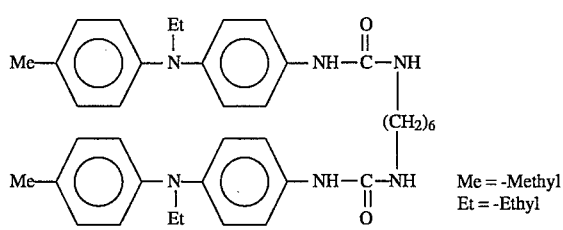 (A192)
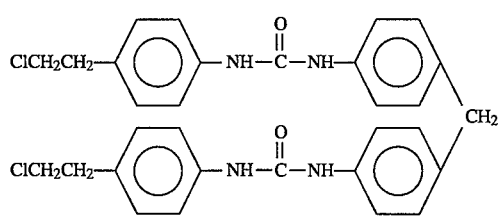 (A193)
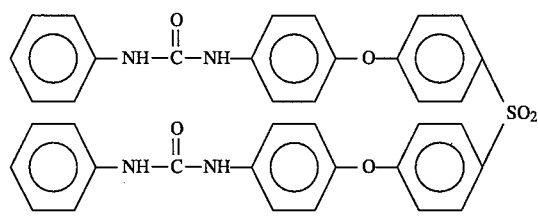 (A194)
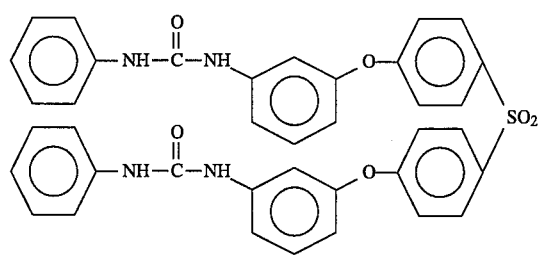 (A195)
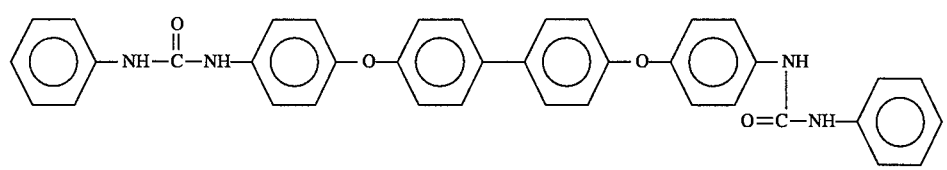 (A196)

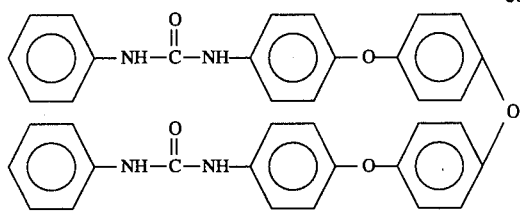 (A197)
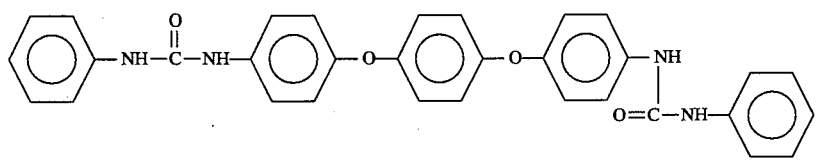 (A198)
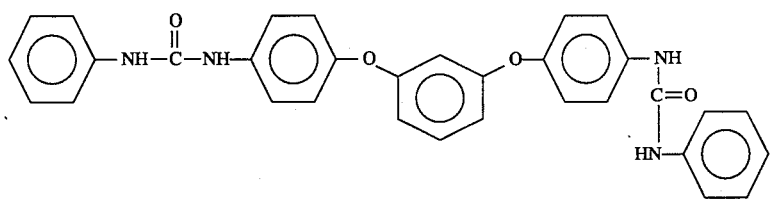 (A199)
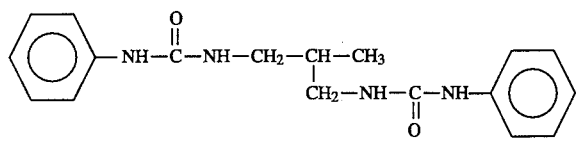 (A200)
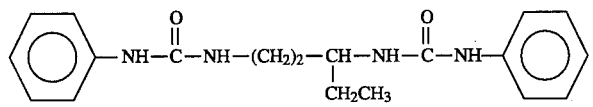 (A201)
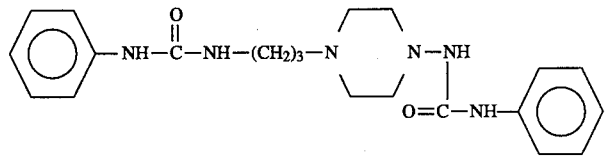 (A202)
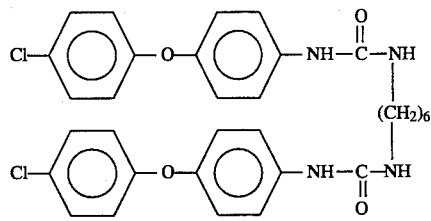 (A203)
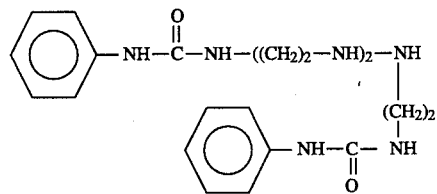 (A204)
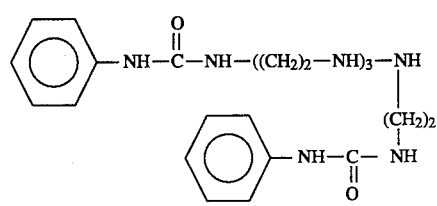 (A205)

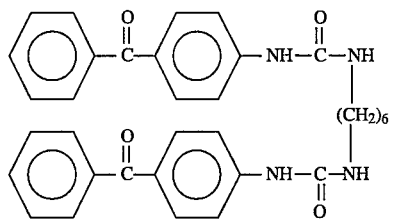 (A206)

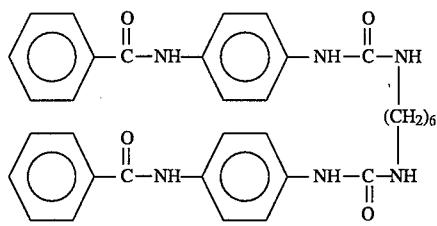 (A207)

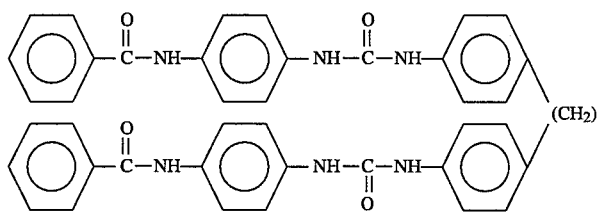 (A208)

The joint group is to be appropriately selected according to the melting point, decomposition temperature, solubility to solvents, and the like of the urea compound, and to the property of the thermal recording sheets using the urea compound as a developer, and then is not specifically limited. For example, for the thermal recording sheet using the dimerized urea compound of Formula (3), the joint groups are broadly divided by the joint group as follows:

(1) A thermal recording sheet having a thermal recording layer containing at least one urea compound (e.g. A1–A12, A31–A62) where in the joint group is a straight-chain alkylene group having 1 to 12 carbon atoms.

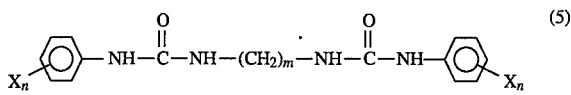 (5)

(wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group n is an integer from 1 to 3, and m is an integer from 1 to 12).

(2) A thermal recording sheet having a thermal recording layer containing at least one urea compound (e.g. A13–A18) wherein the joint group is an alkylene group having 1 to 15 carbon atoms and having a branched chain.

(3) A thermal recording sheet having a thermal recording layer containing at least one urea compound (e.g. A19–A23, A27–A30) wherein the joint group is a plurality of alkylenes group having 1 to 12 carbon atoms linked with nitrogen or oxygen.

The plurality of alkylenes linked with nitrogen or oxygen include the following structures:

Linked with nitrogen:

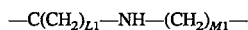

wherein L1 is an integer from 1 to 11, M1 is an integer from 1 to 11, and L1+M1=2 to 12.

wherein L2 is an integer from 1 to 10, M2 is an integer from 1 to 10, N2 is an integer from 1 to 10, and L2+M2+N2=3 to 12.

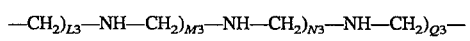

wherein L3 is an integer from 1 to 9, M3 is an integer from 1 to 9, N3 is an integer from 1 to 9, Q3 is an integer from 1 to 9, and L3+M3+N3+Q3=4 to 12.

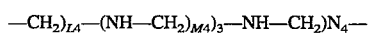

wherein L4 is an integer from 1 to 8, M4 is an integer from 1 to 2, N4 is an integer from 1 to 8, and L4+3×M4+N4=5 to 12

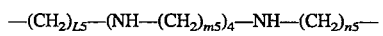

( wherein L5 is an integer from 1 to 7, M5 is an integer from 1 to 2, N5 is an integer from 1 to 7, and L5+4×M5+N5=6 to 12.)

Linked with oxygen

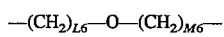

wherein L6 is an integer from 1 to 11, M6 is an integer from 1 to 11, and L6+M6=2 to 12.

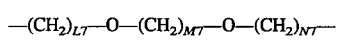

(wherein L7 is an integer from 1 to 10, M7 is an integer from 1 to 10, N7 is an integer from 1 to 10, and L7+M7+N7=3 to

12.)

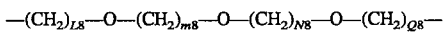

wherein L8 is an integer from 1 to 9, M8 is an integer from 1 to 9, N8 is an integer from 1 to 9, Q8 is an integer from 1 to 9, and L8+M8"N8+Q8=4 to 12.

When linked with nitrogen, hydrogen linked to the nitrogen atom of the joint group may be substituted with alkyl group of 1 to 12 carbon atoms or aryl group of 6 to 18 carbon atoms or unsubstituted.

(4) A thermal recording sheet having a thermal recording layer containing at least one urea compound (e.g. A103, A104, A114, A115) wherein the joint group is a substituted or unsubstituted cycloalkyl group having 1 to 20 carbon atoms.

This is further divided into one in which the two phenylurea structures are linked directly to a single cycloalkyl ring, one in which the two phenylurea structures are linked to two cycloalkyls, and one in which the two phenylurea structures are linked to alkylene group bonded to a cycloalkyl ring.

(5) A thermal recording sheet having a thermal recording layer containing at least one urea compound (e.g. A87–A102, A107, A108) wherein the joint group is a group having one substituted or unsubstituted aromatic ring and having 1 to 20 carbon atoms.

This is further divided into one in which the two phenylurea structures are linked directly to one aromatic ring, and one in which the two phenylurea structures are linked to alkylene group bonded to an aromatic ring. The aromatic ring can be benzene ring, pyridine ring, naphthalene ring, and the like, and benzene ring is considered to be preferable in view of availability of the raw material.

(6) A thermal recording sheet having a thermal recording layer containing at least one urea compound (e.g. A63–A86, A197–A199) wherein the joint group is a group having at least two substituted or unsubstituted aromatic rings and having 1 to 30 carbon atoms.

This is further divided into those having two aromatic rings, three aromatic rings, and four aromatic rings. Also in this case, benzene ring is preferable in view of availability of the raw material.

However, of the urea compounds of this category, the urea compound of Formula (6), that is, the joint group is diphenylene group, is considered to be carefully used for general applications in view of safety of the raw material for synthesis.

(7) A thermal recording sheet having a thermal recording layer containing at least one urea compound (e.g. A109–A111) wherein the joint group contains a substituted or unsubstituted piperazine ring and having 4 to 12 carbon atoms.

In terms of the recording density, a case where the joint group is a straight-chain alkylene group having 1 to 12 carbon atoms, a case where the joint group is an alkylene group having 1 to 15 carbon atoms and having a branched chain, and a case where the joint group is a plurality of alkylene group having 1 to 12 carbon atoms linked with nitrogen or oxygen atom are preferable. And in view of the total balance of the recording density and heat resistance, a case where the joint group is a straight-chain alkylene group having 1 to 12 carbon atoms, and a case where the joint group is an alkylene group having 1 to 15 carbon atoms are more preferable.

Further, the sustituent (X) of phenyl urea structure of Formula (1) is also to be selected according to the melting point, decomposition temperature, the easy handling in the synthesis, and solubility in solvents of the urea compound, and the property of the thermal recording materials using the urea compound (recording density, heat resistance, and so on.), as for joint group, and is not specifically limited. For instance, in view of the recording density, a case where the substituted is hydrogen atom (that is, unsubstituted) and a case where the substituent is an electorophilic group (e.g. halogenated alkyl group, nitro group, cyano group, halogen atom) are preferable. And in terms of the cost and safety of the urea compound, a case where the substituted is hydrogen atom is considered to be more preferable.

On the other hand, the thermal recording sheet using the dimerized urea compound of Formula (2) or (3) or that using the trimerized urea compound of Formula (4) of the present invention is superior in ground color stability to heat and solvents as basic properties. That is, even when the thermal recording sheet is placed in a high-temperature environment of above 120° C, the ground color of the recording surface is substantially unchanged. For example, the exemplified compound A8 does not develop a color even at 150° C. which is the highest temperature of static color development. However, when the compound is applied with high energy of the thermal head of normally at 200° to 300° C., it develops a dense color. For the heat resistance of ground color, in the common sense on thermal recording sheet in the past, it cannot be considered to be possible that no color is developed when the surface of the thermal recording sheet is applied with a heat block at above 120° C., but can be

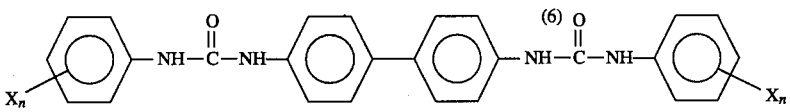

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group n is an integer from 1 to 3).

recorded with a practically usable density by a thermal head, and such a material has been unknown.

Since the thermal recording sheet of the present invention has the above-described high heat resistance, it can be heat laminated with a plastic film on the recording surface after recording, used as an electrophotographic transfer sheet to be thermally fixed by coating a toner on the surface of the recording layer, and thermally fixed by coating a toner on the recording surface of the recorded sheet.

Further, the thermal recording sheet of the present invention is very easy in controlling the production process. In the production of conventional thermal recording sheet, the drying process after coating the recording layer requires very strict temperature control to prevent the coated surface from color development, limiting high-speed coating. However, since the thermal recording sheet of the present invention does not develop the ground color even when applied with hot air at 120° C. it can be dried at a high temperature, and the control range of the drying temperature can be substantially expanded, a remarkable improvement in productivity can be expected.

The thermal recording sheet of the present invention, possibly due to very low solubility in organic solvents of the dimerized or trimerized urea compound used, causes almost no change in ground color even when contacted with solvents other than alcohol. Therefore, it can be recorded by oil ink on the recording surface.

The inventors have conducted studies on the thermal decomposition temperature and solubility to solvents of a number of dimerized or trimerized urea compounds, and have found that the thermal decomposition temperature and solubility to solvents can be controlled by selecting the joint group. By further studies, they have found a recording sheet in which the recorded image can be erased by applying an amount of heat by a heat roll, a thermal head, a drying oven or a hot stamp, by irradiation with light by a laser or a halogen lamp, or by contacting with alcoholic solvents such as methanol or ethanol, and the erased surface can be recorded again by applying a thermal head or laser, that is, a reversible recording sheet. This is achieved by using at least one dimerized urea compound of Formula (2) or (3) or a trimerized urea compound of Formula (4) as a color developer.

A reversible recording sheet which is good in erasability by heat roll uses a color developer of a urea compound of Formula (5) (e.g. A1– A12) wherein the joint group is straight-chain alkylene group having 1 to 12 carbon atoms.

The thermal recording sheet using these urea compounds as a color developer, after being color developed by a thermal head or the like, can be erased by contacting with a heat roll at 100° to 200° C., and the erased surface can be recorded again by a thermal head or the like. For example, good results are obtained with a recording sheet which ues the exemplified compounds such as A3, A4, A5, A6, A8, A10, A14, and A49 as a color developer.

The dimerized urea compound of Formula (3) and the trimerized urea compound of Formula (4), from another point of view, are considered as compounds in which the phenylurea structures are appropriately separated by the joint group. From this point of view, a urea compound which is superior in erasing ground color under a heating condition different from recording by a thermal head is preferably a dimerized urea compound in which the phenylurea structures are separated by 3 to 8 carbon atoms.

The dimerized or trimerized urea compound used in the present invention alone in itself has a high color developing ability as a color developer in the thermal recording sheet, and the surface of the substrate coated with the compound along with the electron-donating dye precursor does not substantially develop a color even at 120° C., showing basic properties of superior solvent resistance of ground color. In addition, depending on the selected joint group, some types of the urea compound of the present invention have a reversible recording function (color developing/erasing). Such characteristics are new characteristics which have been unknown in the past, and these urea compounds are superior materials that have both color developing and erasing functions though it is a single color developer.

In a general method for producing the thermal recording sheet of the present invention, (a) the dye precursor and (b) the dimerized or trimerized urea compound as a color developer are individually dispersed along with a binder having a dispersing function and, as necessary, mixed with additives such as a filler, a slip agent, and the like to obtain a coating color, which is coated on a substrate by a conventional method known in the art, and then dried. The dimerized or trimerized urea compounds of the present invention can be used alone or in combination.

The dye precursor used in the thermal recording sheet of the present invention can be those which are known to the public in the area of thermal recording, and is not specifically limited, but triphenylmethane type leuco dyes, fluorane type leuco dyes, fluorene type leuco dyes, and the like are preferable. Typical dye precursors are shown below:

3,3-Bis(4'-dimethylaminophenyl)-6-dimethylaminophthalide [alias Crystal Violet Lactone (CVL)]
3,3-Bis(4'-dimethylaminophenyl)-6-pyrrolidylphthalide
3,3-Bis(4'-dimethylaminophenyl)phthalide [alias Malachite Green Lactone (MGL)]
Tris(4-(dimethylamino)phenyl)methane (alias Leuco Crystal Violet (LCV))
3-Dimethylamino-6-methyl-7-(m-trifluoromethylanilino) fluorane
3-Diethylamino-6-methyl-fluorane
3-Diethylamino-7-methyl-fluorane
3-Diethylamino-7-chloro fluorane
3-Diethylamino-6-methyl-7-chlorofluorane
3-Diethylamino-6-methyl-7-anilinofluorane
3-Diethylamino-6-methyl-7-p-methylanilinofluorane
3-Diethylamino-6-methyl-7-(o,p-dimethylanilin)fluorane
3-Diethylamino-6-methyl-7-(m-trifluoromethylanilino)fluorane
3-Diethylamino-6-methyl-7-(o-chloroanilino)fluorane
3-Diethylamino-6-methyl-7-(p-chloroanilino)fluorane
3-Diethylamino-6-methyl-7-(o-fluoroanilino)fluorane
3-Diethylamino-6-methyl-7-(p-n-butylanilino)fluorane
3-Diethylamino-6-methyl-7-n-octylaminofluorane
3-Diethylamino-6-chloro -7-anilinofluorane
3-Diethylamino-6-ethoxyethyl-7-anilinofluorane
3-Diethylamino-benzo[a]fluorane
3-Diethylamino-benzo[c]fluorane
3-Diethylamino-6-methyl-7-benzylaminofluorane
3-Diethylamino-6-methyl-7-dibenzylaminofluorane
3-Diethylamino-7-di(p-methylbenzyl)aminofluorane
3-Diethylamino-6-methyl-7-diphenylmethylaminofluorane
3-Diethylamino-7-dinaphthylmethylaminofluorane
10-Diethylamino-4-dimethylaminobenzo[a ]fluorane
3-Dibutylamino-6-methylfluorane
3-Dibutylamino-6-methyl-7-chlorofluorane
3-Dibutyiamino-6-methyl-7-anilinofluorane
3-Dibutylamino-6-methyl-7-p-methylanilinofluorane
3-Dibutylamino-6-methyl-7-(o,p-dimethylanilino)fluorane
3-Dibutylamino-6-methyl-7-(m-trifluoromethylanilino)fluorane
3-Dibutylamino-6-methyl-7-(o-chloroanilino)fluorane
3-Dibutylamino-6-methyl-7-(p-chloroanilino)fluorane
3-Dibutylamino-6-methyl-7-(o-fluoroanilino)fluorane
3-Dibutylamino-6-methyl-7-)p-n-butylanilino)fluorane
3-Dibutylamino-6-methyl-7-n-octylaminofluorane
3-Dibutylamino-6-chloro-7-anilinofluorane
3-Dibutylamino-6-ethoxyethyl-7-anilinofluorane
3-Di-n-pentylamino-6-methyl-7-anilinofluorane
3-Di-n-pentylamino-6-methyl-7-(o,p-dimethylanilino)fluorane
3-Di-n-pentylamino-6-methyl-7-(m-trifluoromethylanilino)fluorane
3-Di-n-pentylamino-6-methyl-7-(o-chloroanilino)fluorane 3-Di-n-pentylamino-6-methyl-7-(p-chloroanilino)fluorane
3-Di-n-pentylamino-6-methyl-7-(o-fluoroanilino)fluorane
3-Pyrrolidino-6-methyl-7-anilinofluorane
3-Piperidino-6-methyl-7-anilinofluorane
3-(N-methyl-N-n-propylamino)-6-methyl-7-anilinofluorane
3-(N-ethyl-N-n-propylamino)-6-methyl-7-anilinofluorane
3-(N-ethyl-N-isopropylamino)-6-methyl-7-anilinofluorane
3-(N-ethyl-N-n-butylamino)-6-methyl-7-anilinofluorane
3-(N-ethyl-N-isobutylamino)-6-methyl-7-anilinofluorane
3-(N-ethyl-N-n-hexylamino)-6-methyl-7-p-methylanilinofluorane
3-(N-ethyl-N-n-hexylamino)-6-methyl-7-(o,p-dimethylanilino)fluorane
3-(N-ethyl-N-n-hexylamino)-6-methyl-7-(m-trifluoromethylanilino) fluorane
N3-(N-ethyl-N-n-hexylamino)-6-methyl-7-(o-chloroanilino)fluorane
3-(N-ethyl-N-isoamylamino)-6-methyl-7-anilino)fluorane
3-(N-ethyl-N-isoamylamino)-6-chloro-7-anilino)fluorane
3-(N-ethyl-N-3-methylbutylamino)-6-methyl-7-anilino)fluorane
3-(N-ethyl-N-p-toluidino)-6-methyl-7-anilinofluorane
3-(N-ethyl-N-p-toluidino)-6-methyl-7-(p-methylanilino)fluorane
3-(N-ethyl-N-p-toluidino)-6-methyl-7-(o,p-dimethylanilino)fluorane
3-(N-ethyl-N-tetrahydrofurfurylamino)-6-methyl-7-anilinofluorane
3-(N-cyclohexyl-N-methylamino)-6-methyl-7-anilinofluorane
3-(N-cyclohexyl-N-methylamino)-7-anilinofluorane
3-(N-ethyl-N-3-methoxypropylamino)-6-methyl-7-anilinofluorane
3-(N-ethyl-N-3-ethoxypropylamino)-6-methyl-7-anilinofluorane
2-(4-Oxahexyl)-3-dimethylamino-6-methyl-7-anilinofluorane
2-(4-Oxahexyl)-3-diethylamino-6-methyl-7-anilinofluorane
2-(4-Oxahexyl)-3-dipropylamino-6-methyl-7-anilinofluorane
3-(4"-Aminostilbuldyl-4'-amino)-7,8-benzofuran
3,6,6'-Tris(dimethylamino)spiro[fluorene-9,3'-phthalide]
3,6,6'-Tris(diethylamino)spiro[fluorene-9,3'-phthalide]
3-(4-Diethylamino-2-ethoxyphenyl)-3-(1-ethyl-2-methylindol- 3-yl)-4-azaphthalide
3-(4-Diethylamino-2-ethoxyphenyl)-3-(1-octyl-2-methylindol- 3-yl)-4-azaphthalide
3-(4-Diethylamino-2-n-hexylphenyl)-3-(1-ethyl-2-methylindol- 3-yl)-4-azaphthalide
3-(4-Cyclohexylmethylamino-2-methoxyphenyl)-3-(1-ethyl-2-methylindol- 3-yl)-4-azaphthalide
3-(4-Cyclohexylethylamino-2-methoxyphenyl)-3-(1-ethyl-2-methylindol- 3-yl)-4-azaphthalide
3,3-Bis(1-ethyl-2-methylindol-3-yl)phthalide
3,3-Bis(1-methyl-2-octylindol-3-yl)phthalide
3-(1-Ethyl-2-methylindol-3-yl)-3-(1-n-butyl-2-methylindol-3-yl)phthalide
3,7-Bis(dimethylamino)-10-benzoylphenothiazine
3,7-Bis(dimethylamino)-N-[p-N-bis(4,4'-dimethylaminophenyl)methylamino] benzoylphenothiazine
3,7-Bis(dimethylamino)-N-(p-N-bis(4,4'-diethylaminophenyl)methyl)benzoylphenothiazine
3,6-Bis(diethylamino)fluorane-γ-(2'-nitro)anilinolactam
3,6-Bis(diethylamino)fluorane-γ-(3'-nitro)anilinolactam
3,6-Bis(diethylamino)fluorane-γ-(4'-nitro)anilinolactam
3,6-Bis(diethylamino)fluorane-γ-anilinolactam.

These dye precursors may be used alone or as mixtures of two or more types. Since fluorane type dye precursors are particularly high in stability of color development and ground color as basic functions of the thermal recording sheet, they can be preferably used in the present invention. Naturally, when thermal stability is important, a dye precursor which is high in melting point and decomposition temperature is preferable. When the reversible recording function is important, it is preferable to use 3-dimethylamino-7-(m-trifluoromethylanilino)fluorane and the like, which is weak in image stability, can withstand repeated use, and is high in decomposition temperature.

The binder usable in the present invention includes completely hydrolyzed polyvinylacohol having a polymerization degree of 200 to 1900, partially-hydrolyzed polyvinylalcohol, carboxy-modified polyvinylalcohol, amide-modified polyvinylalcohol, sulfonic acid-modified polyvinylalcohol, butyral-modified polyvinylalcohol, other modified polyvinylalcohols, styrene-maleic anhydride copolymer, styrene-butadiene copolymer, cellulose derivatives such as hydroxyethylcellulose, methylcellulose, carboxymethylcellulose, ethylcellulose and acetylcellulose, polyvinylchloride, polyvinylacetate, polyacrylamide, polyacrylic esters, polyvinylbutyral, polystyrene and copolymers thereof, polyamide resins, silicone resins, petroleum resins, terpene resins, ketone resins, and coumarone resins. Of these binders, the polyvinylalcohol type binder is preferable in terms of the dispersibility, binding properties, and thermal stability of ground color. For reversible recording, a binder which can with stand repeated use and is small in degradation is preferable. These binders are used by dissolving in solvents such as water, alcohol, ketone, ester, and hydrocarbon, emulsifying in water or other solvents, or dispersing to a paste form, and can be used in combination according to the quality requirements.

In the present invention, when a thermal recording sheet which is particularly high in thermal stability of ground color is produced, it is better in principle not to use a sensitizer. When a sensitizer is used, it tends to melt at a drying temperature, and causes the dye precursor to react with the color developer to develop the ground color. However, on the other hand, since the sensitizer promotes the erasing function, when importance is attached to the erasing function rather than the thermal stability of ground color, that is, the reversible recording function, a sensitizer may be used. Sensitizers used for this purpose include 2-di(3-methylphenoxy)ethane, p-benzylbiphenyl, β-benzyloxynaphthalene, phenyl 1-hydroxy-2-naphthoate, dibenzylterephthalate, benzyl p-benzyloxybenzoate, diphenylcarbonate, ditolylcarbonate, 4-biphenyl-p-tolylether, m-terphenyl, 1,2-diphenoxyethane, 1,2-bis(m-tolyloxy)ethane, di(p-methylbenzyl)oxalate, and di(p-chlorobenzyl)oxalate.

The filler used in the present invention includes inorganic fillers such as silica, calcium carbonate, kaolin, calcined kaolin, diatomaceous earth, talc, zinc oxide, titanium oxide, zinc hydroxide, and aluminum hydroxide; polystyrene-based organic fillers, styrene/butadiene-based organic fillers, styrene/acrylic-based organic fillers, and hollow organic fillers.

In addition to the above, a release agent such as fatty acid metal salts, a slip agent such as waxes, benzophenoe or benzotriazole type ultraviolet absorbents, a water-resistant agent such as glyoxal, a dispersant, a defoamer, and the like can be used.

Types and ratios of (a) the dye precursor, (2) the dimerized or trimerized urea compound, and other ingredients are determined by the required properties and recording adaptability, and are not specifically limited but, normally, based on one part of the dye precursor, 1 to 8 parts of the dimerized or trimerized urea compound, and 1 to 20 parts of the filler are used, and the binder is used in an amount of 10 to 25% by weight to the total solid. For repeated use such as the reversible recording sheet, it is preferable to use a composition as simple as possible. These materials are finely crushed by a crusher such as a ball mill, an attriter, or a sand grinder, or an appropriate emulsifying apparatus to a particle diameter of several microns or less, a binder and, as necessary, other additives are added to obtain a coating color. The coating color comprising the above composition is coated on a desired substrate such as paper, synthetic paper, non-woven fabrics, plastic films, Diastic sheets, or composite sheets thereof to obtain the objective thermal recording sheet.

Further, an overcoating layer comprising a polymer can be provided on top of the recording layer to enhance the preservability, or an undercoating layer of a polymer containing a filler can be provided under the recording layer to enhance the color developing sensitivity.

The thermal recording sheet of the present invention, utilizing its high ground color stability, may be heat laminated with a plastic film to form a transparent and strong protective coating. For example, even after thermal recording, a heat-resistant card can be easily prepared using a commercial simple laminator.

Of the thermal recording sheets of the present invention, one which has an erasing function is useful as a reversible recording sheet (rewrite or rewritable recording sheet), or as a simple displaying sheet. However, for the latter application, it is necessary to achieve recording and erasing almost simultaneously.

Erasing of the thermal recording sheet of the present invention is achieved by two methods. One method uses a heat roll, a thermal head, a hot stamp, a carbon dioxide laser, a semiconductor laser, sunlight, a halogen lamp, or the like to erase the recorded image by heat. For example, for a heat roll, the erasing temperature is preferably 100° to 200° C. with a feed speed of 8 to 45 mm/sec. The other method uses an alcoholic solvent to erase the recorded image.

The thermal recording sheet of the present invention may contain an optical absorbent which absorbs light to convert it to heat in the thermal recording layer, for use as an optical recording sheet. The optical absorbent can be a substance which absorbs wavelengths of various light sources, and is not specifically limited.

For example, for a recording light source having continuous wavelength, such as a stroboflash, the optical absorbent can be a heat reaction product of thiourea derivative/copper compound described in Japanese OPIs 2-206583 and 5-30954, graphite, copper sulfide, molybdenum trisulfide, black titanium, and the like described in Japanese OPI 3-86580, or carbon black.

On the other hand, when a semiconductor laser is used as a recording light source, the optical absorbent can be polymethine type dyes (cyanine dyes); azolenium type dyes, pylylium type dyes, thiopylylium type dyes, squalylium type dyes, chroconium type dyes, dithiol complexes, mercaptophenol-metal complex type dyes, mercaptonaphthol-metal complex type dyes, phthalocyanine type dyes, naphthalocyanine type dyes, triarylmethane type dyes, immonium type dyes, diimmonium type dyes, naphthoquinone type dyes, anthraquinone type dyes, and metal complex type dyes. Further, the optical absorbents listed for a light source having continuous wavelength can also be used as well.

Specifically, a near infrared absorption dyes described in "Color chemical dictionary" (The society of Synthetic Organic Chemistry, CMC-publishing company, 1988, P196–200). "Kagaku to Kogyo" (Vol. 5, 1986, p376–389). Japanese OPIs 61-69991, and 61-246391, and U.S. Pat. Nos. 3,251,881, 35,570,122, 3,575,871, and 3,637,769; 1,1,5,5-tetrakis(p-dimethylaminophenyl)-3-methoxy-1,4-pentadien (or its cation form), 1,1,5,5-tetrakis(p-diethylaminophenyl)-3-methoxy-1,4-pentadien (or its cation form); toluenedithiol nickel complex, 4-tert-butyl-1,2-benzenedithiol nickel complex, bisdithiobenzilnickelcomplex, bis(4-ethyldithiobenzil)nickel complex, and so on. These optical absorbents can be used alone or as mixture of two or more types.

These optical absorbents may be used by: (a) a method in which the optical absorbent is simply mixed in the materials necessary for the thermal recording sheet, (b) a method in which the optical absorbent is previously melted and mixed, and dissolved or dispersed to be used, as described in Japanese OPI 2-217287, or (c) a method in which the optical absorbent is previously dissolved or dispersed by a solvent in the materials necessary for the thermal recording sheet, the solvent is removed from the mixture, and then used. The optical absorbent may also be co-dispersed with the color developer with the dre precuesor, with the color developer and the sensitizer or with the dye precursor and the sensitizer.

The thermal recording sheet of the present invention, even when combined with the optical absorbent to form an optical recording sheet, is substantially unchanged in the basic properties (e.g. ground color stability such as heat resistance and solvent resistance). Even the optical recording sheet can be heat laminated or toner recorded. This is also true for the additional functions (reversible recording). However, when a sensitizer is used, the heat resistance tends to be impaired. The thermal recording sheet laminated with the plastic film, which contains the optical absorbant, can be recorded by light and as laser-light.

The novel dimerized or trimerized urea compound according to the present invention is a color developer which is superior in color development and ground color stability to heat and solvents as basic functions, and some types have a reversible recording function. The reason for the superior ground color stability and the reversible recording function has yet to clarified. However, this is considered as follows:

Depending on the condition, the dimerized or trimerized urea compound of the present invention changes in structure as shown below. Since this change is a phenomenon similar to the keto/enol tautomerism, and is referred here to as keto-form and enol-form for convenience.

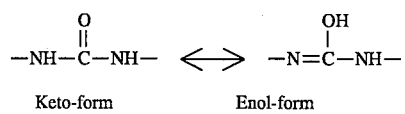

Keto-form        Enol-form

It is considered that the dimerized or trimerized urea compound must have the enol-form to function as a color developer. Since enol-formation requires a high temperature, and the thermal head instantaneously provides a high temperature of 200 to 3000 C., the urea compound contacting with the thermal head undergoes enol-formation to have a color developing function, opening the lactone ring of the dye precursor to develop a color. Therefore, the urea compound does not change until the enol-formation temperature is reached, does not react with the dye precursor, and the ground color remains unchanged. This would be the reason for the high heat resistance. Further, since the dimerized or trimerized urea compound increases the number of active hydrogens compared to a monourea compound, a good color developing function is obtained.

On the other hand, if the thus produced enol-form converts to the keto-form for some reason, erasing would occur. Therefore, when the compound is provided with an appropriate temperature and head, or contacts with an alcoholic solvent, keto-formation occurs, resulting in erasing. Since enol-formation and keto-formation occur under quite different conditions, the enol-form and the keto-form can be repeated under the individual conditions, thereby enabling reversible recording.

The reason why the ground color is not changed by writing with an oil ink is considered as due to the fact that the dimerized or trimerized urea compound of the present invention is very low in solubility in the solvent used in the oil ink, and the dye precursor and the color developer are not substantially mixed with each other even when contacting the solvent.

DETAILED DESCRIPTION OF PREFERRED EMBODIMENTS

EXAMPLES

Synthesis of dimerized and trimerized urea compounds

Dimerized and trimerized urea compounds were synthesized by the following synthetic methods. General synthetic methods are shown below.

Synthesis Example 1

A monoisocyanate compound (2.2 eq.) was dissolved in ethyl acetate (or acetone). Into the solution, a solution of a diamine compound (1.0 eq,) in ethyl acetate (or acetone) was dropped. After stirring for a predetermined time, generated precipitate was filtered, and washed with ethyl acetate, n-hexane, hot water, and methanol in this order until 1 spot was obtained on TLC (thin layer chromatograph) to obtain a urea compound.

Synthesis Example 2

A diisocyanate compound (1.0 eq.) was dissolved in ethyl acetate (or acetone). Into the solution, a solution of a monoamine compound (2.2 eq.) in ethyl acetate (or acetone) was dropped. After stirring for a predetermined time, generated precipitate was filtered, and washed with ethyl acetate, n-hexane, hot water, and methanol in this order until 1 spot was obtained on TLC to obtain a urea compound.

Synthesis Example 3

A triisocyanate compound (1.0 eq.) was dissolved in ethyl acetate (or acetone). Into the solution, a solution of a monoamine compound (3.3 eq.) in ethyl acetate (or acetone) was dropped. After stirring for a predetermined time, generated precipitate was filtered, and washed with ethyl acetate, n-hexane, hot water, and methanol in this order until 1 spot was obtained on TLC to obtain a urea compound.

Production of thermal recording sheet

In the following description, unless otherwise noted, part and % indicate part by weight and % by weight, respectively.

EXAMPLES 1–48

As shown below, thermal recording sheets were produced using 3-N,N-diethylamino-6-methyl-7-anilinofluorane (ODB) as a dye precursor and the dimerized urea compound (or trimerized urea compound) of the present invention (Table 1, Table 2, Table 3) as a developer.

Specifically, a color developer dispersion (Solution A) and a dye precursor dispersion (Solution B) of the following compositions were milled by a sand grinder to an average particle diameter of 1 micron.

| Solution A: color developer dispersion | |
|---|---|
| Inventive dimerized urea compound (or trimerized urea compound) | 6.0 parts |
| 10% Aqueous polyvinylalcohol solution | 18.8 |
| Water | 11.2 |
| Solution B: dye precursor dispersion | |
| 3-N,N-diethylamino-6-methyl-7-anilinofluorane (ODB) | 2.0 parts |
| 10% Aqueous polyvinylalcohol solution | 4.6 |
| Water | 2.6 |

Then, the Solution A (color developer dispersion), the Solution B (dMe precursor dispersion), and a kaolin clam dispersion were mixed in the following ratio to obtain a coating color.

| | |
|---|---|
| Solution A (color developer dispersion) | 36.0 parts |
| Solution B (dye precursor dispersion) | 9.2 |
| Kaolin clay (50% dispersion) | 12.0 |

The coating color was coated on one side of a 50 g/m$^2$ base paper to a coating coverage of 6.0 g/m$^2$, dried, and supercalendered to a flatness of 500 to 60 seconds to obtain a thermal recording sheet.

EXAMPLES 49–56

Thermal recording sheets were produced using the dye precursors other than ODB and using the same procedure as in Examples 1–48 (Table 5).

| Dye precursor | |
|---|---|
| ODB-2: | 3-N,N-dibutylamino-6-methyl-7-anilinofluorane |
| CVL: | 3,3-bis(p-dimethylaminophenyl)-6-methyl-7-nilinophthalide |
| NEW-Blue: | 3-(4-diethylamino-2-ethoxyphenyl)-3-(1-ethyl-2-methylindol-3-yl)-4-azaphthalide |
| I-red: | 3,3-bis(1-ethyl-2-methylindol-3-yl)phthalide |

First, a dye precursor dispersion (Solution C) of the following composition was milled by a sand grinder to an average particle diameter of 1 micron.

| Solution C: dye precursor dispersion | |
|---|---|
| Above dye precursor | 2.0 parts |
| 10% Aqueous polyvinylalcohol solution | 4.6 |
| Water | 2.6 |

Then, the color developer dispersion used in Example 4 (or Example 6), Solution C, and a kaolin clay dispersion were mixed in the following ratio to obtain a coating color.

| | |
|---|---|
| Color developer dispersion of Example 6 using the compound A8 (or color developer dispersion of Example 4 using the compound A6) | 36.0 part |
| Solution C: dye precursor dispersion | 9.2 |
| Kaolin clay (50% dispersion) | 12.0 |

The coating color was coated on one side of a 50 g/m² base paper in an amount of 6.0 g/m² and dried, and the sheet was supercalendered to a flatness of 500 to 600 seconds to obtain a thermal recording sheet.

Comparative Examples 1–7

Thermal recording sheets for comparative tests were prepared using the known compounds shown below as color developers and using the same procedure as in Examples 1–48.

TABLE 4

Known color developer compounds

Bisphenol A (B1)
Bisphenol S (B2)
4-Hydroxy-4'-iso-propoxydiphenylsulfone (B3)
4-Hydroxy-4'-n-propoxydiphenylsulfone (B4)
Phenylurea (B5) described in Japanese OPI 58-211496
Dimerized urea (B6) described in Japanese OPI 5-147357
Amidephenol derivative (B7)

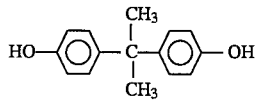

(B1)

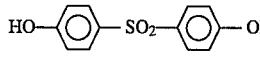

(B2)

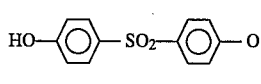

(B3)

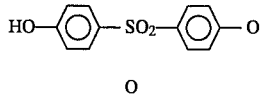

(B4)

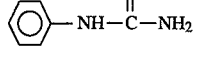

(B5)

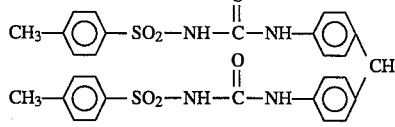

(B6)

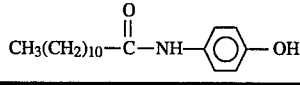

(B7)

Specifically, dispersions of the above individual known color developer compounds of the following composition were milled by a sand grinder to an average particle diameter of 1 micron.

| Solution D: color developer dispersion | |
|---|---|
| Known color developer compound (B1–B7) | 6.0 parts |

| Solution D: color developer dispersion | |
|---|---|
| 10% Aqueous polyvinylalcohol solution | 18.8 |
| Water | 11.2 |

Then, Solution D (color developer dispersion), the dye precursor (ODB) dispersion (Solution B) used in Examples 1–48, and a kaolin clay dispersion were mixed in the following ratio to obtain a coating color.

| | |
|---|---|
| Solution D: color developer dispersion | 36.0 parts |
| Solution B: dye precursor dispersion (ODB dispersion) | 9.2 |
| Kaolin clay (50% dispersion) | 12.0 |

The coating color was coated on one side of a 50 g/m² base paper in an amount of 6.0 g/m² and dried, and the sheet was supercalendered to a flatness of 500 to 600 seconds to obtain a thermal recording sheet.

Comparative Examples 8–9

Thermal recording sheets for comparative tests were prepared using hisphenol A as a color developer, and ODB-2 and NEW-BLUE and using the same procedure as in Examples 49–56. (Table 5)

Evaluation of Thermal Recording Sheets

The resulting thermal recording sheets were tested for basic properties by a recordability test using a thermal printer, a ground color thermal stability test, and an oil ink adaptability test.

Recordability test (dynamic color developing density)

To test the recording adaptability, the thermal recording sheet was recorded using a word processor printer (RUPO-90F: Trade mark of word processor made by Toshiba co,. ltd.) at a maximum energy, and the recorded portion was measured by a Macbeth densitometer (RD-914, an amber filter used. Hereinafter density was measured in this condition). In this case, the greater the Macbeth value, the higher the recording density and the better the recording adaptability.

Ground color thermal stability test (static color developing density)

To test the thermal stability of ground color, the recording sheet was pressed against a hot plate heated individually at 90° C., 120° C. and 150° C. at a pressure of 10 g/cm² for 5 seconds, and the treated sheet was measured by a Macbeth densitometer. In this case, the smaller the Macbeth value, the smaller the coloring of ground color and the higher the thermal stability of ground color. Oil ink adaptability test (discoloration of ground color by oil ink):

The recording sheet was written with a felt pen of red oil ink Magic INK No. 900/Teranishi Kagaku co,. ltd., and visually measured for a degree of discoloration compared to a conventional red ink.

A: No discoloration
B: Little discoloration
C: Slight discoloration
D: Considerable discoloration The evaluation results of the basic properties of Examples 1–56 using the dimerized or trimerized urea compounds of the present invention as color developers, and Comparative Examples 1–9 using the conventional color developer compound are shown in Tables 1 to 5.

TABLE 1

| Entry | Color developer | Ground color before recording | Recordability test | Thermal stability of ground color | | | Oil ink adaptability |
|---|---|---|---|---|---|---|---|
| | | | | 90° C. | 120° C. | 150° C. | |
| Ex. 1 | A3 | 0.03 | 1.34 | 0.03 | 0.03 | 0.04 | A |
| Ex. 2 | A4 | 0.02 | 1.12 | 0.02 | 0.03 | 0.04 | A |
| Ex. 3 | A5 | 0.03 | 1.28 | 0.03 | 0.03 | 0.05 | A |
| Ex. 4 | A6 | 0.02 | 1.26 | 0.02 | 0.03 | 0.04 | A |
| Ex. 5 | A7 | 0.03 | 1.35 | 0.03 | 0.04 | 0.05 | A |
| Ex. 6 | A8 | 0.02 | 1.21 | 0.02 | 0.03 | 0.05 | A |
| Ex. 7 | A10 | 0.04 | 1.15 | 0.04 | 0.04 | 0.04 | A |
| Ex. 8 | A12 | 0.02 | 1.16 | 0.02 | 0.03 | 0.08 | A |
| Ex. 9 | A14 | 0.06 | 1.28 | 0.06 | 0.06 | 0.06 | A |
| Ex. 10 | A15 | 0.02 | 1.16 | 0.03 | 0.03 | 0.05 | A |
| Ex. 11 | A16 | 0.03 | 1.07 | 0.03 | 0.04 | 0.06 | A |
| Ex. 12 | A17 | 0.02 | 1.29 | 0.02 | 0.04 | 0.24 | A |
| Ex. 13 | A19 | 0.03 | 1.31 | 0.03 | 0.05 | 0.74 | A |
| Ex. 14 | A28 | 0.03 | 1.28 | 0.03 | 0.04 | 0.79 | A |
| Ex. 15 | A31 | 0.03 | 1.15 | 0.03 | 0.04 | 0.05 | A |
| Ex. 16 | A32 | 0.03 | 1.24 | 0.03 | 0.04 | 0.05 | A |

Note: ODB used as a dye

TABLE 2

| Entry | Color developer | Ground color before recording | Recordability test | Thermal stability of ground color | | | Oil ink adaptability |
|---|---|---|---|---|---|---|---|
| | | | | 90° C. | 120° C. | 150° C. | |
| Ex. 17 | A33 | 0.04 | 0.92 | 0.04 | 0.05 | 0.06 | A |
| Ex. 18 | A34 | 0.03 | 0.91 | 0.03 | 0.04 | 0.05 | A |
| Ex. 19 | A49 | 0.04 | 1.22 | 0.04 | 0.04 | 0.05 | A |
| Ex. 20 | A50 | 0.03 | 1.16 | 0.03 | 0.03 | 0.05 | A |
| Ex. 21 | A51 | 0.03 | 0.98 | 0.03 | 0.04 | 0.05 | A |
| Ex. 22 | A52 | 0.04 | 1.11 | 0.04 | 0.04 | 0.05 | A |
| Ex. 23 | A53 | 0.03 | 1.10 | 0.03 | 0.03 | 0.05 | A |
| Ex. 24 | A54 | 0.05 | 1.35 | 0.05 | 0.06 | 0.16 | A |
| Ex. 25 | A55 | 0.03 | 1.23 | 0.03 | 0.04 | 0.05 | A |
| Ex. 26 | A56 | 0.04 | 1.24 | 0.04 | 0.04 | 0.06 | A |
| Ex. 27 | A63 | 0.03 | 0.82 | 0.03 | 0.04 | 0.05 | A |
| Ex. 28 | A64 | 0.04 | 0.87 | 0.05 | 0.05 | 0.05 | A |
| Ex. 29 | A65 | 0.10 | 0.83 | 0.10 | 0.12 | 0.02 | A |
| Ex. 30 | A66 | 0.04 | 0.86 | 0.04 | 0.05 | 0.06 | A |
| Ex. 31 | A68 | 0.03 | 0.81 | 0.03 | 0.04 | 0.05 | A |
| Ex. 32 | A69 | 0.04 | 0.93 | 0.04 | 0.05 | 0.07 | A |

Note: ODB used as a dye

TABLE 3

| Entry | Color developer | Ground color before recording | Recordability test | Thermal stability of ground color | | | Oil ink adaptability |
|---|---|---|---|---|---|---|---|
| | | | | 90° C. | 120° C. | 150° C. | |
| Ex. 33 | A79 | 0.05 | 0.85 | 0.05 | 0.06 | 0.12 | A |
| Ex. 34 | A82 | 0.12 | 0.80 | 0.12 | 0.13 | 0.14 | A |
| Ex. 35 | A90 | 0.03 | 0.85 | 0.03 | 0.04 | 0.05 | A |
| Ex. 36 | A92 | 0.03 | 0.85 | 0.03 | 0.03 | 0.03 | A |
| Ex. 37 | A100 | 0.02 | 1.14 | 0.02 | 0.04 | 0.05 | A |
| Ex. 38 | A101 | 0.03 | 1.09 | 0.03 | 0.04 | 0.05 | A |
| Ex. 39 | A103 | 0.02 | 0.90 | 0.03 | 0.04 | 0.06 | A |
| Ex. 40 | A104 | 0.02 | 0.92 | 0.02 | 0.04 | 0.28 | A |
| Ex. 41 | A111 | 0.03 | 1.00 | 0.03 | 0.04 | 0.05 | A |
| Ex. 42 | A112 | 0.04 | 0.81 | 0.04 | 0.04 | 0.05 | A |
| Ex. 43 | A120 | 0.05 | 0.82 | 0.05 | 0.05 | 0.08 | A |
| Ex. 44 | A124 | 0.02 | 0.74 | 0.03 | 0.04 | 0.05 | A |
| Ex. 45 | A186 | 0.04 | 1.07 | 0.04 | 0.04 | 0.04 | A |
| Ex. 46 | A200 | 0.02 | 1.16 | 0.02 | 0.03 | 0.05 | A |
| Ex. 47 | A201 | 0.03 | 1.03 | 0.03 | 0.04 | 0.05 | A |
| Ex. 48 | A203 | 0.04 | 1.03 | 0.05 | 0.07 | 0.09 | A |

Note: ODB used as a dye

TABLE 4

| Entry | Color developer | Ground color before recording | Recordability test | Thermal stability of ground color | | | Oil ink adaptability |
|---|---|---|---|---|---|---|---|
| | | | | 90° C. | 120° C. | 150° C. | |
| Comp. Ex. 1 | B1 | 0.06 | 1.44 | 0.21 | 1.51 | 1.53 | D |
| Comp. Ex. 2 | B2 | 0.06 | 1.30 | 0.08 | 0.21 | 0.58 | D |
| Comp. Ex. 3 | B3 | 0.04 | 1.50 | 0.13 | 1.55 | 1.56 | D |
| Comp. Ex. 4 | B4 | 0.04 | 1.52 | 0.04 | 0.13 | 1.55 | D |
| Comp. Ex. 5 | B5 | 0.03 | 1.01 | 0.04 | 0.06 | 0.94 | A |
| Comp. Ex. 6 | B6 | 0.06 | 1.14 | 0.07 | 0.11 | 1.02 | A |
| Comp. Ex. 7 | B7 | 0.07 | 0.79 | 0.08 | 0.49 | 0.68 | C |

Note: ODB used as a dye

TABLE 4

| Entry | Dye | Color developer | Ground color before recording | Recordability test | Thermal stability of ground color | | | Oil ink adaptability |
|---|---|---|---|---|---|---|---|---|
| | | | | | 90° C. | 120° C. | 150° C. | |
| Ex. 49 | ODB-2 | A8 | 0.05 | 1.26 | 0.05 | 0.05 | 0.07 | A |
| Ex. 50 | CVL | A8 | 0.03 | 0.82 | 0.03 | 0.04 | 0.05 | A |
| Ex. 51 | NEW-Blue | A8 | 0.07 | 0.98 | 0.07 | 0.08 | 0.10 | A |
| Ex. 52 | I-red | A8 | 0.03 | 1.02 | 0.03 | 0.05 | 0.06 | A |
| Ex. 53 | ODB-2 | A6 | 0.05 | 1.30 | 0.05 | 0.06 | 0.07 | A |
| Ex. 54 | CVL | A6 | 0.04 | 0.84 | 0.04 | 0.05 | 0.06 | A |
| Ex. 55 | NEW-Blue | A6 | 0.08 | 0.90 | 0.08 | 0.09 | 0.09 | A |
| Ex. 56 | I-red | A6 | 0.03 | 0.80 | 0.03 | 0.05 | 0.06 | A |
| Com. Ex. 8 | ODB-2 | B1 | 0.05 | 1.30 | 0.27 | 1.31 | 1.36 | D |
| Com. Ex. 9 | NEW-Blue | B1 | 0.04 | 1.34 | 0.29 | 1.33 | 1.39 | D |

Then, to test for additional properties, the thermal recording sheet was subjected to a heat lamination test and a reversible recording test.

Heat lamination test (preparation of laminated recording sheet)

Using a simple lamination apparatus (MS Pouch H-140/ Meiko Shokai), the thermal recording sheet was put between pouch films to prepare a laminated thermal recording sheet, and the ground color thereof was measured by a Macbeth densitometer. In this case, the smaller the Macbeth value shows the better the ground color stability. In other words, the sheet can be laminated without coloring. The thermal recording sheet using the dimerized or trimerized urea compound of the present invention was able to be laminated with a stable ground color.

Reversible recording test

As in the recordability test, the thermal recording sheet was recorded by a word processor printer, the recorded sheet was passed between 180° C. heat rolls at a speed of 30 mm/sec, and the recorded portion and the ground color portion were measured by a Macbeth densitometer. In this case, the smaller the Macbeth value of the recorded portion shows the higher the erasability. After that, the sheet was again recorded by the word processor printer, and the recorded portion was measured for Macbeth density.

Evaluation results of additional properties of the Examples using the dimerized or trimerized urea compound of the present invention as a color developer and Comparative Examples 1–8 using a known color developer compound are shown in Tables 8 to 9.

TABLE 6

| Entry | Color developer | Heat lamination test | Reversible recordability test | | | Re-recording |
|---|---|---|---|---|---|---|
| | | | Recorded portion | Erasing | | |
| | | | | (Recorded portion) | Ground color) | |
| Ex. 1 | A3 | 0.10 | 1.34 | 0.20 | 0.04 | 1.31 |
| Ex. 2 | A4 | 0.11 | 1.12 | 0.13 | 0.04 | 1.09 |
| Ex. 3 | A5 | 0.12 | 1.28 | 0.18 | 0.04 | 1.24 |
| Ex. 4 | A6 | 0.11 | 1.26 | 0.16 | 0.04 | 1.24 |
| Ex. 5 | A7 | 0.12 | 1.35 | 0.19 | 0.05 | 1.27 |
| Ex. 6 | A8 | 0.11 | 1.21 | 0.14 | 0.04 | 1.19 |
| Ex. 7 | A10 | 0.12 | 1.15 | 0.14 | 0.04 | 1.10 |
| Ex. 8 | A12 | 0.11 | 1.16 | 0.32 | 0.16 | 1.11 |
| Ex. 9 | A14 | 0.14 | 1.28 | 0.13 | 0.06 | 1.20 |
| Ex. 10 | A15 | 0.10 | 1.16 | 0.37 | 0.04 | 1.11 |
| Ex. 15 | A31 | 0.12 | 1.15 | 0.20 | 0.04 | 1.10 |
| Ex. 16 | A32 | 0.12 | 1.24 | 0.19 | 0.04 | 1.18 |
| Ex. 17 | A33 | 0.13 | 0.92 | 0.22 | 0.06 | 0.88 |
| Ex. 18 | A34 | 0.10 | 0.91 | 0.13 | 0.04 | 0.86 |
| Ex. 19 | A49 | 0.14 | 1.22 | 0.19 | 0.04 | 1.19 |

Note: ODB used as a dye

TABLE 7

| Entry | Color developer | Heat lamination test | Reversible recordability test | | | Re-recording |
|---|---|---|---|---|---|---|
| | | | Recorded portion | Erasing (Recorded portion) | Erasing (Ground color) | |
| Ex. 20 | A50 | 0.15 | 1.16 | 0.20 | 0.05 | 1.11 |
| Ex. 21 | A51 | 0.12 | 0.96 | 0.40 | 0.05 | 0.93 |
| Ex. 22 | A52 | 0.13 | 1.11 | 0.22 | 0.04 | 1.05 |
| Ex. 23 | A53 | 0.14 | 1.10 | 0.21 | 0.05 | 1.02 |
| Ex. 25 | A55 | 0.11 | 1.23 | 0.28 | 0.05 | 1.17 |
| Ex. 27 | A63 | 0.13 | 0.82 | 0.50 | 0.06 | 0.78 |
| Ex. 28 | A64 | 0.14 | 0.87 | 0.50 | 0.05 | 0.83 |
| Ex. 31 | A68 | 0.12 | 0.81 | 0.44 | 0.05 | 0.79 |
| Ex. 33 | A79 | 0.12 | 0.85 | 0.40 | 0.09 | 0.81 |
| Ex. 35 | A90 | 0.12 | 0.79 | 0.35 | 0.05 | 0.72 |
| Ex. 37 | A100 | 0.12 | 1.04 | 0.44 | 0.06 | 0.99 |
| Ex. 38 | A101 | 0.12 | 1.09 | 0.43 | 0.04 | 1.01 |
| Ex. 43 | A120 | 0.16 | 0.72 | 0.30 | 0.08 | 0.70 |

Note: ODB used as a dye

TABLE 8

| Entry | Color developer | Heat lamination | Reversible recordability test | | | Re-recording |
|---|---|---|---|---|---|---|
| | | | Recorded portion | Erasing (Recorded portion) | Erasing (Ground color) | |
| Comp. Ex. 1 | B1 | 1.96 | 1.44 | 1.58 | 1.50 | — |
| Comp. Ex. 2 | B2 | 0.37 | 1.30 | 1.43 | 0.93 | — |
| Comp. Ex. 3 | B3 | 1.86 | 1.50 | 1.57 | 1.54 | — |
| Comp. Ex. 4 | B4 | 0.28 | 1.52 | 1.54 | 1.49 | — |
| Comp. Ex. 5 | B5 | 0.29 | 1.03 | 1.05 | 0.96 | — |
| Comp. Ex. 6 | B6 | 0.28 | 1.14 | 1.11 | 0.99 | — |
| Comp. Ex. 7 | B7 | 0.64 | 0.79 | 0.44 | 0.15 | 0.73 |

Note: ODB used as a dye

TABLE 9

| Entry | Dye | Color developer | Heat lamination | Revers. recordability test | | | Re-recording |
|---|---|---|---|---|---|---|---|
| | | | | Recorded-Erasing | (Recorded portion) | Ground color | |
| Ex. 49 | ODB-2 | A8 | 0.09 | 1.26 | 0.10 | 0.05 | 1.25 |
| Ex. 50 | CVL | A8 | 0.10 | 0.82 | 0.11 | 0.05 | 0.80 |
| Ex. 51 | NEW-BLUE | A8 | 0.10 | 0.98 | 0.09 | 0.05 | 0.98 |
| Ex. 52 | 1-red | A8 | 0.11 | 1.02 | 0.15 | 0.06 | 0.98 |
| Comp. Ex. 8 | ODB-2 | B1 | 1.84 | 1.30 | 1.56 | 1.48 | — |
| Comp. Ex. 9 | NEW-BLUE | B1 | 1.79 | 1.34 | 1.49 | 1.43 | — |

EXAMPLE 57

The thermal recording sheet of Example 1 was subjected to 100 repetitions of a reversibility test by a heat roll. The Macbeth densities of the recorded portion and ground color of the 100th time were 1.20 and 0.07, respectively.

EXAMPLE 58

The thermal recording sheet of Example 3 was subjected to 100 repetitions of a reversibility test by a heat roll. The Macbeth densities of the recorded portion and ground color of the 100th time were 1.18 and 0.07, respectively.

EXAMPLE 59

The thermal recording sheet of Example 4 was subjected to 100 repetitions of a reversibility test by a heat roll. The Macbeth densities of the recorded portion and ground color of the 100th time were 1.04 and 0.08, respectively.

EXAMPLE 60

The thermal recording sheet of Example 6 was subjected to 100 repetitions of a reversibility test by a heat roll. The Macbeth densities of the recorded portion and ground color of the 100th time were 1.09 and 0.08, respectively.

EXAMPLE 61

The thermal recording sheet of Example 49 was subjected to 100 repetitions of a reversibility test by a heat roll. The Macbeth densities of the recorded portion and ground color of the 100th time were 1.12 and 0.07, respectively.

EXAMPLE 62

The thermal recording sheet of Example 51 was subjected to 100 repetitions of a reversibility test by a heat roll. The Macbeth densities of the recorded portion and ground color of the 100th time were 0.94 and 0.09, respectively.

EXAMPLE 63

The thermal recording sheet of Example 56 was subjected to 50 repetitions of a reversibility test by a heat roll. The Macbeth densities of the recorded portion and ground color of the 50th time were 0.76 and 0.11, respectively.

EXAMPLE 64

The thermal recording sheet of Example 3 was recorded by a word processor printer, and the recorded surface was wiped out with ethanol. The recorded portion had a Macbeth density of 0.23.

EXAMPLE 65

The thermal recording sheet of Example 9 was recorded by a word processor printer, and the recorded surface was wiped out with ethanol. The recorded portion had a Macbeth density of 0.16.

EXAMPLE 66

The thermal recording sheet of Example 18 was recorded by a word processor printer, and the recorded surface was wiped out with ethanol. The recorded portion had a Macbeth density of 0.19.

EXAMPLE 67

The thermal recording sheet of Example 3 was toner recorded by a copier (NP6060/Canon co,. ltd). No change in the ground color was noted.

EXAMPLE 68

The thermal recording sheet of Example 5 was toner recorded by a copier (NP6060/Canon co,. ltd). No change in the ground color was noted.

EXAMPLE 69

The thermal recording sheet of Example 28 was toner recorded by a copier (NP6060/Canon co,. ltd). No change in the ground color was noted.

EXAMPLE 70

The thermal recording sheet of Example 53 was toner recorded by a copier (NP6060/Canon co,. ltd). No change in the ground color was noted. Production of Thermal recording sheet containing the optical absorbent.

EXAMPLES 71–77

As described above, an optical recording sheet was produced using 3-N,N-diethylamino-6-methyl-7-anilinofluorane (ODB) as a dye precursor, the dimerized urea compound (or the trimerized urea compound) of the present invention as a color developer, and a heat melt (optical absorbent A) of a bis-dithiobenzylnickel complex and a sensitizer as an optical absorbent. (Table 10)

Specifically, 94 parts of 4-biphenyl-9-tolylether was mixed with B parts of bi-dithiobenzylnickel complex, heated to 100° to 150° C. to melt, and then crushed to obtain an optical absorbent. An optical absorbent dispersion of the following composition was milled by a sand grinder to an average particle diameter of 1 micron.

| (Solution E: optical absorbent dispersion) | |
|---|---|
| Optical absorbent | 4.0 parts |
| 10% Aqueous polyvinylalcohol solution | 10.0 |
| Water | 6.0. |

Then, the color developer dispersion (Solution A) used in Examples 1–48, the dye precursor (ODB) dispersion (Solution B) used in Examples 1–48, Solution E (optical absorbent dispersion), and a kaolin clay dispersion were mixed in the following ratio to obtain a coating color.

| | |
|---|---|
| Solution A (color developer dispersion) | 36.0 parts |
| Solution B (dye precursor dispersion) | 9.2 |
| Solution E (optical absorbent dispersion) | 20.0 |
| Kaolin clay (50% dispersion) | 12.0 |

The coating color was coated on one side of a 50 g/m² base paper in an amount of 6.0 g/m² and dried, and the sheet was supercalendered to a flatness of 500 to 600 seconds to obtain an optical recording sheet.

EXAMPLE 78–81

An optical recording sheet was produced using NK-2612 (Nippon Kanko Shikiso Kenkyusho) (optical absorbent B) as an optical absorbent in place of the heat melt of bis-dithiobenzylnickel complex and a sensitizer. (Table 10)

First, the following aqueous optical absorbent solution was prepared.

| (Solution F: aqueous optical absorbent solution) | |
|---|---|
| NK-2612 | 0.04 parts |
| Water | 3.96. |

Then, the color developer dispersion (Solution A) used in Examples 1–48, the dye precursor (ODB) dispersion (Solution B) used in Examples 1–48, Solution E (optical absorbent dispersion), and a kaolin clay dispersion were mixed in the following ratio to obtain a coating color.

| | |
|---|---|
| Solution A (color developer dispersion) | 36.0 parts |
| Solution B (dye precursor dispersion) | 9.2 |
| Soluti;on F (optical absorbent solution) | 4.0 |
| Kaolin clay (50% dispersion) | 12.0 |

The coating color was coated on one side of a 50 g/m² base paper in an amount of 6.0 g/m² and dried, and the sheet was supercalendered to a flatness of 500 to 600 seconds to obtain an optical recording sheet.

EXAMPLES 82–84

An optical recording sheet was produced using toluene-dithiolnickel complex (optical absorbent C) as an optical absorbent in place of the heat melt of bis-dithiobenzylnickel complex and a sensitizer.

First, an optical absorbent dispersion (Solution G) was milled by a sand grinder to an average particle diameter of 1 micron.

| Solution G (optical absorbent color developer dispersion) | |
| --- | --- |
| Compound A6 (or compound A8 or A66) | 6.0 parts |
| Toluenedithiolnickel complex | 1.0 |
| 10% Aqueous polyvinylalcohol solution | 18.8 |
| Water | 10.2. |

Then, the optical absorbent color developer dispersion (Solution G), the dye precursor (ODB) dispersion (Solution B) used in Examples 1 –48, and a kaolin clay dispersion were mixed in the following ratio to obtain a coating color.

| | |
| --- | --- |
| Solution G (optical absorbent color developer dispersion) | 36.0 parts |
| Solution B (dye precursor dispersion) | 9.2 |
| Kaolin clay (50% dispersion) | 12.0 |

The coating color was coated on one side of a 50 g/m² base paper in an amount of 6.0 g/m² and dried, and the sheet was supercalendered to a flatness of 500 to 600 seconds to obtain an optical recording sheet.

EXAMPLES 85–86

Using ODB-2 or NEW-Blue as a dye precursor in place of ODB, the same procedure as in Examples 7114 77 was used to obtain an optical recording sheet.

EXAMPLES 87–88

Using ODB-2 or NEW-Blue as a dye precursor in place of ODB, the same procedure as in Examples 78–81 was used to obtain an optical recording sheet.

EXAMPLES 89–90

Using NEW-Blue or I-red as a dye precursor in place of ODB, the same procedure as in Examples 82–84 was used to obtain an optical recording sheet. Evaluation of optical recording sheets The resulting optical recording sheets were subjected to a recordability test. Recordability test (optical recording):

Using a laser plotter described in Japanese OPI 3-239598, the optical recording sheet was irradiated with a laser light, and the recorded portion was measured by a Macbeth densitometer. Using a 30 mW semiconductor laser LT015MD (Sharp) with an oscillation wavelength of 830 nm as a recording light sources, an aspheric plastic lens AP4545 (Konica) with a numerical aperture of 0.45 and a focal length of 4.5 mm as an optical converging lens, a recording speed of 50 mm/sec, and a recording interval of 50 microns, a 1 cm square overall recording was obtained. The evaluation results are shown in Table 10.

TABLE 10

| Entry | Color developer | Dye | Optical absorbent | Recordability test |
| --- | --- | --- | --- | --- |
| Example 71 | Compound A3 | ODB | Absorbent A | 1.38 |
| Example 72 | Compound A6 | ODB | Absorbent A | 1.28 |
| Example 73 | Compound A8 | ODB | Absorbent A | 1.25 |
| Example 74 | Compound A19 | ODB | Absorbent A | 1.40 |

TABLE 10-continued

| Entry | Color developer | Dye | Optical absorbent | Recordability test |
| --- | --- | --- | --- | --- |
| Example 75 | Compound A39 | ODB | Absorbent A | 1.00 |
| Example 76 | Compound A49 | ODB | Absorbent A | 1.22 |
| Example 77 | Compound A68 | ODB | Absorbent A | 1.02 |
| Example 78 | Compound A6 | ODB | Absorbent B | 1.26 |
| Example 79 | Compound A7 | ODB | Absorbent B | 1.33 |
| Example 80 | Compound A16 | ODB | Absorbent B | 1.10 |
| Example 81 | Compound A63 | ODB | Absorbent B | 1.04 |
| Example 82 | Compound A6 | ODB | Absorbent C | 1.27 |
| Example 83 | Compound A8 | ODB | Absorbent C | 1.26 |
| Example 84 | Compound A66 | ODB | Absorbent C | 1.01 |
| Example 85 | Compound A6 | ODB | Absorbent A | 1.27 |
| Example 86 | Compound A6 | ODB | Absorbent A | 1.02 |
| Example 87 | Compound A6 | ODB | Absorbent B | 1.26 |
| Example 88 | Compound A6 | ODB | Absorbent B | 1.00 |
| Example 89 | Compound A6 | ODB | Absorbent C | 1.01 |
| Example 90 | Compound A8 | ODB | Absorbent C | 0.98 |

Absorbent A: bis-dithiobenzylnickel complex/sensitizer
Absorbent B: NK-2612
Absorbent C: toluenedithiolnickel complex As described above, it can be seen that the dimerized or trimerized urea compound of the present invention is an epoch-making color developer that can provide a recording with a practical image density by a thermal head or the like while without a substantial change in ground color at environmental temperatures of 120° to 150° C. Therefore, the present invention has the following effects.

(1) A thermal recording sheet superior in storage stability such as heat resistance and solvent resistance compared to conventional thermal recording sheets.

(2) The thermal recording sheet can be used under severe conditions (e.g. at temperatures of 90°–150° C.) at which conventional products could not be used.

(3) Since the thermal recording sheet does not undergo discoloration when written with an oil ink, it can be freely written using these writing means.

(4) The thermal recording sheet can be simply heat laminated by a simple laminator or the like. Cards and the like can also be easily prepared.

(5) The thermal recording sheet can be toner recorded since the ground color is stable even when passed through a heat roll.

Further, the thermal recording sheet having an erasing function has the following advantages:

(6) A new recording system, which enables repeated color recording and erasing, which leads to resource-saving.

(7) Some types of the sheet can be erased merely by passing through a heat roll, without strict temperature control.

(8) Unlike liquid crystals, the thermal recording sheet can be used a simple display means that can be recorded and erased using different thermal energies.

The thermal recording sheet of the present invention can also be incorporated with an optical absorbent for use as an optical recording sheet having similar effects.

We claim:

1. A thermal recording sheet having a thermal recording layer containing a colorless or pale colored dye precursor and a color developer reactable with said dye precursor upon heating to develop a color, wherein said color developer is a urea compound having at least two groups of Formula (1) in the molecule, and the thermal recording layer contains at least one of said urea compound:

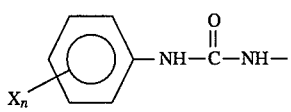

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group or hydrogen group.

2. A thermal recording sheet having a thermal recording layer containing a colorless or pale colored dye precursor and a color developer reactable with said dye precursor upon heating to develop a color, wherein said color developer is a urea compound of Formula (2), (3), or (4), and the thermal recording layer contains at least one of said urea compounds:

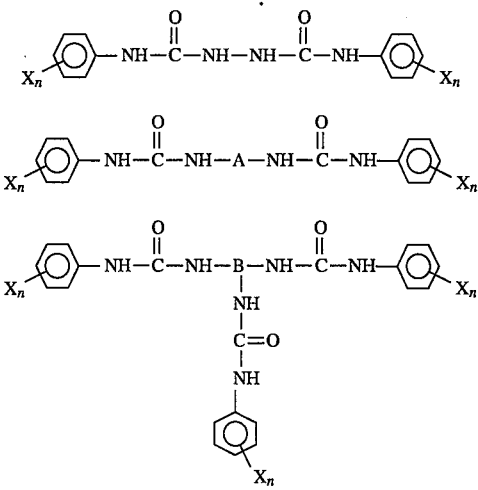

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group, A denotes a divalent group comprising 30 or less carbon atoms, and B denotes a trivalent group comprising 30 or less carbon atoms, n is an integer from 1 to 3.

3. The thermal recording sheet of claim 2, wherein the divalent group (A) of said color developer of Formula (3) is an alkylene group having 1 to 12 carbon atoms and having a branched chain.

4. The thermal recording sheet of claim 2, wherein the divalent group (A) of said color developer of Formula (3) is a plurality of alkylenes group having 1 to 12 carbon atoms linked with nitrogen or oxygen.

5. The thermal recording sheet of claim 2, wherein the divalent group (A) of said color developer of Formula (3) is a group containing at least one substituted or unsubstituted cycloalkyl group having 1 to 20 carbon atoms.

6. The thermal recording sheet of claim 2, wherein the divalent group (A) of said color developer of Formula (3) is a group having one substituted or unsubstituted aromatic ring and having 1 to 20 carbon atoms.

7. The thermal recording sheet of claim 2, wherein the divalent group (A) of said color developer of Formula (3) is a group having at least two substituted or unsubstituted aromatic rings and having 1 to 30 carbon atoms.

8. The thermal recording sheet of claim 2, wherein the divalent group (A) of said color developer of Formula (3) is a group containing a substituted or unsubstituted piperazine ring and having 4 to 12 carbon atoms.

9. A thermal recording sheet having a thermal recording layer containing a colorless or pale colored dye precursor and a color developer reactable with said dye precursor upon heating to develop a color, wherein said color developer is a urea compound of Formula (5), and the thermal recording layer contains at least one of said urea compound:

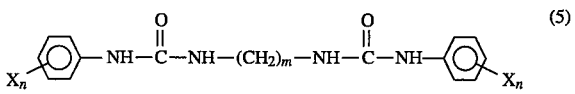

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group, n is an integer from 1 to 3, and m is an integer from 1 to 12.

10. A thermal recording card comprising the thermal recording sheet of claim 2 or 9.

11. A reversible recording method comprising the steps of: recording on the thermal recording sheet of claim 2 or 9 erasing the recorded image by applying heat to the recorded portion, and again thermally recording.

12. A reversible recording method comprising the steps of: recording on the thermal recording sheet of claim 2 or 9, contacting the recorded portion with an alcoholic solvent to erase the recorded image, and again thermally recording.

13. A thermal recording sheet having a thermal recording layer containing a colorless or pale colored dye precursor and a color developer reactable with said dye precursor upon heating to develop a color, wherein said color developer is a urea compound of Formula (2), and the thermal recording layer contains at least one of said urea compound:

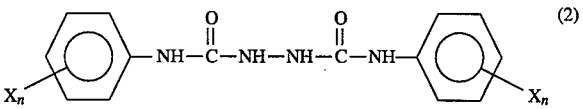

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group.

14. A thermal recording sheet having a thermal recording layer containing a colorless or pale colored dye precursor and a color developer reactable with said dye precursor upon heating to develop a color, wherein said color developer is a urea compound of Formula (3), and the thermal recording layer contains at least one of said urea compound:

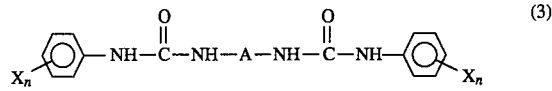

(3)

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group, A denotes a divalent group comprising 30 or less carbon atoms, and n is an integer from 1 to 3.

15. A thermal recording sheet having a thermal recording layer containing a colorless or pale colored dye precursor and a color developer reactable with said dye precursor upon heating to develop a color, wherein said color developer is a urea compound of Formula (4), and the thermal recording layer contains at least one of said urea compound:

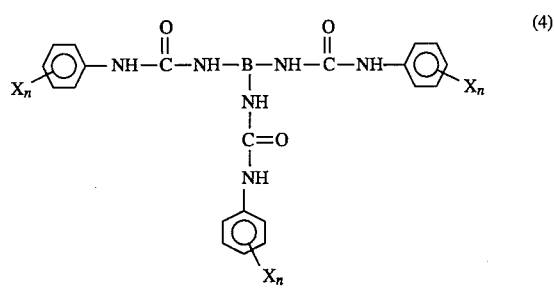

(4)

wherein X is alkyl group having 1 to 12 carbon atoms, halogenated alkyl group having 1 to 6 carbon atoms, aralkyl group having 7 to 14 carbon atoms, alkoxy group having 1 to 12 carbon atoms, aryloxy group having 6 to 12 carbon atoms, alkoxycarbonyl group having 1 to 12 carbon atoms, acyl group having 1 to 12 carbon atoms, dialkylamino group having 1 to 12 carbon atoms, arylalkylamino group having 7 to 12 carbon atoms, arylamino group having 6 to 12 carbon atoms, acylamino group having 1 to 12 carbon atoms, nitro group, cyano group, halogen group, or hydrogen group, B denotes a trivalent group comprising 30 or less carbon atoms, and n is an integer from 1 to 3.

* * * * *